United States Patent
Romanov et al.

(10) Patent No.: US 11,066,410 B2
(45) Date of Patent: Jul. 20, 2021

(54) FUSED TRIAZOLO-PYRIMIDINE COMPOUNDS HAVING USEFUL PHARMACEUTICAL APPLICATION

(71) Applicant: NANOSYN, INC., Santa Clara, CA (US)

(72) Inventors: Sergei Romanov, Chapel Hill, NC (US); Robert Greenhouse, Newark, CA (US); Nikolai Sepetov, Los Gatos, CA (US)

(73) Assignee: 3100 Central Expressway LLC, Santa Clara, CA (US)

( * ) Notice: Subject to any disclaimer, the term of this patent is extended or adjusted under 35 U.S.C. 154(b) by 0 days.

(21) Appl. No.: 16/496,943

(22) PCT Filed: Mar. 23, 2018

(86) PCT No.: PCT/US2018/024060
§ 371 (c)(1),
(2) Date: Sep. 23, 2019

(87) PCT Pub. No.: WO2018/175906
PCT Pub. Date: Sep. 27, 2018

(65) Prior Publication Data
US 2020/0079780 A1    Mar. 12, 2020

Related U.S. Application Data

(60) Provisional application No. 62/601,501, filed on Mar. 24, 2017.

(51) Int. Cl.
C07D 487/04    (2006.01)
A61P 35/00    (2006.01)
C07D 519/00    (2006.01)

(52) U.S. Cl.
CPC .......... C07D 487/04 (2013.01); A61P 35/00 (2018.01); C07D 519/00 (2013.01)

(58) Field of Classification Search
CPC .................. C07D 487/04; A61K 31/5377
USPC .................. 544/118, 254; 514/233.2, 259.31
See application file for complete search history.

(56) References Cited

U.S. PATENT DOCUMENTS

| | | |
|---|---|---|
| 2007/0112006 A1 | 5/2007 | Schiemann et al. |
| 2007/0275961 A1 | 11/2007 | Bower et al. |
| 2008/0070932 A1 | 3/2008 | Vu et al. |

FOREIGN PATENT DOCUMENTS

| | | | |
|---|---|---|---|
| CN | 105963300 A | 9/2016 | |
| JP | H04-99775 A | 3/1992 | |
| WO | WO 1999/043678 A1 | 9/1999 | |
| WO | WO2004092171 | * 10/2004 | ........... C07D 487/00 |
| WO | WO 2016/073877 A1 | 5/2016 | |
| WO | WO 2017/040971 A1 | 3/2017 | |
| WO | WO 2018/175906 A1 | 9/2018 | |

OTHER PUBLICATIONS

International Search Report from International Application No. PCT/US2018/024060 dated Aug. 8, 2018, application now published as International Publication No. WO2018/175906 dated Sep. 27, 2018.

Hayakawa et al., "Structure-activity relationship study, target identification, and pharmacological characterization of a small molecular IL-12/23 inhibitor, APY" Bioorganic & Medicinal Chemistry, vol. 22, No. 11, pp. 3021-3029 (2014).

Vu et al., "Studies on adenosine A"2"a 1,4, receptor antagonists: comparison of three 12-15 core heterocycles", Biorganic & Medicinal Chemistry Letters, vol. 14, No. 19, pp. 4831-4834 (2004).

* cited by examiner

*Primary Examiner* — Jeffrey H Murray
(74) *Attorney, Agent, or Firm* — McDermott Will & Emery LLP; Judy M. Mohr; Brennen P. Baylor

(57) ABSTRACT

A compound and/or a pharmaceutically acceptable salt thereof has the following formula A: These compounds can be PIKfyve kinase inhibitors.

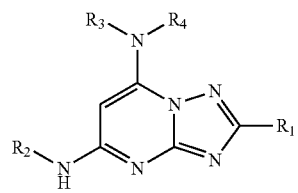

20 Claims, 5 Drawing Sheets

FUSED TRIAZOLO-PYRIMIDINE COMPOUNDS HAVING USEFUL PHARMACEUTICAL APPLICATION

CROSS-REFERENCE TO RELATED APPLICATIONS

This application is a U.S. National Stage Application under 35 U.S.C. § 371 of International Patent Application No. PCT/US2018/024060, filed Mar. 23, 2018, which claims the benefit of priority to U.S. Provisional Patent Application No. 62/601,501, filed Mar. 24, 2017, each of which is incorporated herein by reference in its entirety.

TECHNICAL FIELD

The present disclosure is directed to compounds and/or pharmaceutically acceptable salts thereof which can be PIKfyve kinase inhibitors and useful for the treatment of diseases such as cancers and autoimmune disorders.

BACKGROUND

PIKfyve is a phosphoinositide kinase that phosphorylates PtdIns(3)P at the 5-position of the inositol ring to produce phosphatidylinositol 3,5-bisphosphate (PtdIns(3,5)P2).

PIKfyve kinase is the mammalian orthologue of yeast Fab1 and was first discovered in mammalian cells (Shisheva et al., "Cloning, characterization, and expression of a novel Zn2+-binding FYVE finger-containing phosphoinositide kinase in insulin-sensitive cells," *Mol. Cell. Biol.* 19 (1), pp. 623-34, 1999). cDNA and protein for human PYKfyve was subsequently cloned and characterized (Cabezas et al., "Cloning and subcellular localization of a human phosphatidylinositol 3-phosphate 5-kinase, PIKfyve/Fab1.", *Gene,* 371 (1), pp. 34-41, 2006). Human PIKfyve gene is located at chromosome 2, locus 2q34. The protein comprises four major domains: 1) PtdIns(3)P-binding FYVE domain (amino acid residues 150 to 219), 2) membrane-binding DEP domain (residues 365 to 440), 3) chaperonin-like domain (residues 559 to 1064) and 4) catalytic phosphoinositide kinase homology domain (residues 1791 to 2085). Intracellular localization of PIKfyve protein is mostly restricted to the membranes of late and early endosomes. Biochemically, PIKfyve demonstrates strong preference for phosphatidylinositol (PtdIns) over phosphoinositides (PI) substrates and generates two products identified as PtdIns 5-P and PtdIns 3,5-P2 (Sbrissa et al., "A mammalian ortholog of yeast Fab1p lipid kinase, synthesizes 5-phosphoinositides. Effect of insulin", *J. Biol. Chem.,* 274 (31), pp. 21589-97, 1999).

The PtdIns 3,5-P2 produced by PIKfyve is essential for maintaining late endocytic membrane integrity (Ikonomov et. al., "Functional dissection of lipid and protein kinase signals of PIKfyve reveals the role of PtdIns 3,5-P2 production for endomembrane integrity", *J. Biol. Chem.,* 277 (11), pp. 9206-11, 2002). In addition to PtdIns, PIKfyve was reported to possess protein kinase activity and can undergo auto-phosphorylation (Sbrissa et al., "PIKfyve lipid kinase is a protein kinase: downregulation of 5'-phosphoinositide product formation by autophosphorylation", *Biochemistry,* 39 (51), pp. 15980-9, 2000).

PIKfyve signaling pathway was reported to regulate multiple biological processes, mostly through well documented role in endosomal trafficking. One important aspect of PIKfyve biology is its involvement in Toll-like receptor signaling—a key component of cellular innate immunity system, Thus, inhibition of IL12/23 secretion in response to TLR agonists by a small molecule compound apilimod was recently attributed to the compound's ability to inhibit PtdIns-kinase activity of the PIKfyve (Cai et al., "PIKfyve, a class III PI kinase, is the target of the small molecular IL-12/IL-23 inhibitor apilimod and a player in Toll-like receptor signaling", *Chem. Biol.,* 20 (7), pp. 912-921, 2013). Of note, the apilimod is also being investigated as a pharmacological agent in clinical trials for patients with Crohn's disease or rheumatoid arthritis.

Deregulated IL12/IL23 cytokine production was implicated into various inflammatory disease pathologies including inflammatory bowel diseases, psoriasis, rheumatoid arthritis, and multiple sclerosis. Recent studies demonstrate that yet another small molecule inhibitor of IL12/IL23 production, APY0201, is a highly selective inhibitor of PIKfyve (Hayakawa et al., "Structure-activity relationship study, target identification, and pharmacological characterization of a small molecular IL-12/23 inhibitor, APY0201", *Bioorg. Med. Chem.,* 22 (11), pp. 3021-9, 2014). In addition, two new small molecule inhibitors of IL-12 production by mouse macrophages, AS2677131 and AS2795440, also have been shown to selectively inhibit PIKfyve kinase (Terajima et al., "Inhibition of c-Rel DNA binding is critical for the anti-inflammatory effects of novel PIKfyve inhibitor", *Eur. J Pharmacol.,* 780, pp. 93-105, 2016). AS2677131 also prevented development of rheumatoid arthritis in experimental animals.

PIKfyve also represents a pharmacological target in cancer. Because of its involvement in the cytosolic vacuolation and lysosomal fusion reactions which are essential for autophagy and macropinosome degradation, inhibition of PIKfyve can lead to the obstruction of lysosome dependent nutrient generation pathways operating in some cancer types (Kim et al., "Targeting cancer metabolism by simultaneously disrupting parallel nutrient access pathways", *J. Clin. Invest.,* 126 (11), pp. 4088-4102, 2016). Recent studies demonstrate that PIKfive (through PtdIns 5-Ps) can regulate cancer cell mobility and invasiveness by activating the Rho family GTPase Rac1 (Dupuis-Coronas et al., "The nucleophosmin-anaplastic lymphoma kinase oncogene interacts, activates, and uses the kinase PIKfyve to increase invasiveness", *J. Biol. Chem.,* 286 (37), pp. 32105-14, 2011; Oppelt et al., "PIKfyve, MTMR3 and their product PtdIns5P regulate cancer cell migration and invasion through activation of Rac1", *Biochem. J.,* 461 (3), pp. 383-90, 2014). A small molecule inhibitor of PIKfyve, YM201636, strongly inhibited migration of cancer cells in in vitro models (Oppelt et al). A role of the PIKfyve inhibition for anti-cancer therapy is further supported by anti-proliferative effects of apilimod observed in several cancer cell lines. The PIKfyve inhibitor demonstrated selective nanomolar cytotoxicity in B-cell non-Hodgkin lymphomas, but not in normal cells (Gayle et al., "Identification of apilimod as a first-in-class PIKfyve kinase inhibitor for treatment of B-cell non-Hodgkin lymphoma", *Blood,* doi: 10.1182/blood-2016-09-736892, 2017).

The scientific research together supports selection of PIKfyve as a therapeutic target for pharmacological intervention in several disease conditions including cancer and autoimmune disorders such as rheumatoid arthritis, inflammatory bowel diseases, psoriasis, and multiple sclerosis. Therefore, the utility of small molecule compounds described in current invention should be viewed by a knowledgeable in the art as applicable but not limited to the above mentioned disorders.

SUMMARY

In one aspect, 2,5,7-trisubstituted-[1,2,4]triazolo[1,5-a]pyrimidines, such as a compound of Formula I and/or a pharmaceutically acceptable salt thereof is provided:

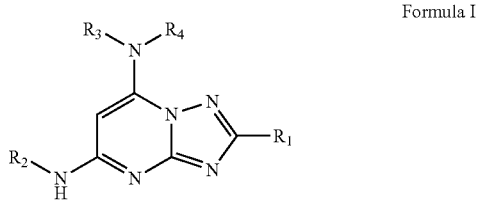

Formula I wherein
$R_1$ is optionally substituted alkyl, optionally substituted cycloalkyl, optionally substituted heterocyclyl, optionally substituted aryl, or optionally substituted heteroaryl, provided $R_1$ is not cyclohexyl,
$R_2$ is alkyl, aryl, heteroaryl, —N═CH-alkyl, —N═CH-aryl or —N═CH-heteroaryl, in which each of the alkyl, aryl and heteroaryl is optionally substituted,
$R_3$ and $R_4$ are independently H, optionally substituted alkyl, optionally substituted aryl, optionally substituted heteroaryl, optionally substituted cycloalkyl, or optionally substituted heterocyclyl, provided that when $R_3$ and $R_4$ are such, $R_1$ is not $C_{1-3}$ alkyl; or $R_3$ and $R_4$ together with the nitrogen to which they are attached form an optionally substituted heterocyclyl.

The compound of Formula I and/or a pharmaceutically acceptable salt thereof can inhibit PIKfyve kinase.

In another aspect, a pharmaceutical composition comprising a compound of Formula I and/or a pharmaceutically acceptable salt thereof and a pharmaceutically acceptable carrier is provided.

In another aspect, a method of treating an individual suffering from a disease treatable by inhibition of PIKfyve kinase is provided. The method comprises administering to the individual in need thereof a therapeutically effective amount of a pharmaceutical composition comprising a compound of Formula I and/or a pharmaceutically acceptable salt thereof, wherein such administration reduces or eliminates a symptom associated with the disease.

DETAILED DESCRIPTION

Figure 1A:
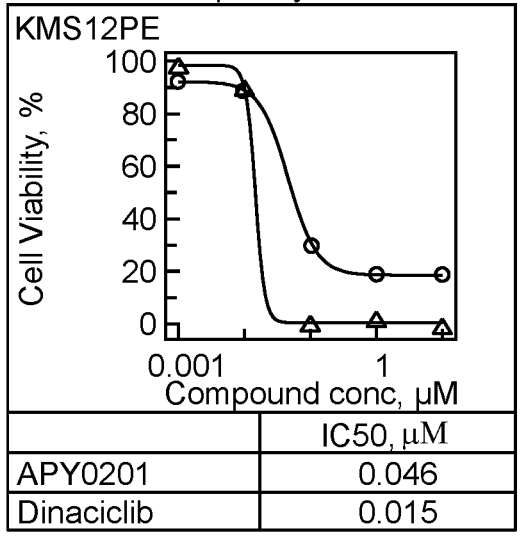
FIG. 1A-1D show that PIKfyve inhibitor selectively inhibited growth of cancer cell lines.
Figure 1B:
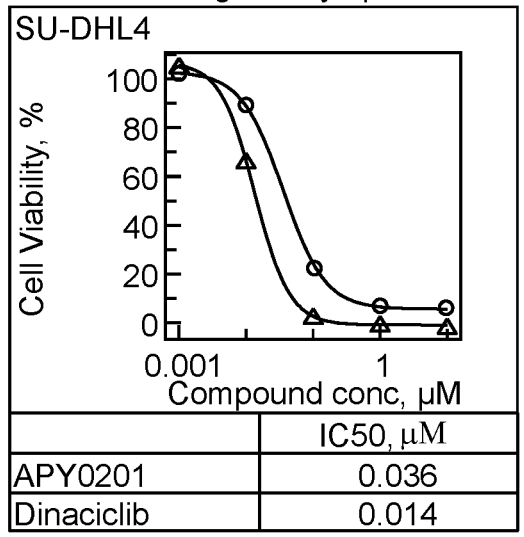
Figure 1C:
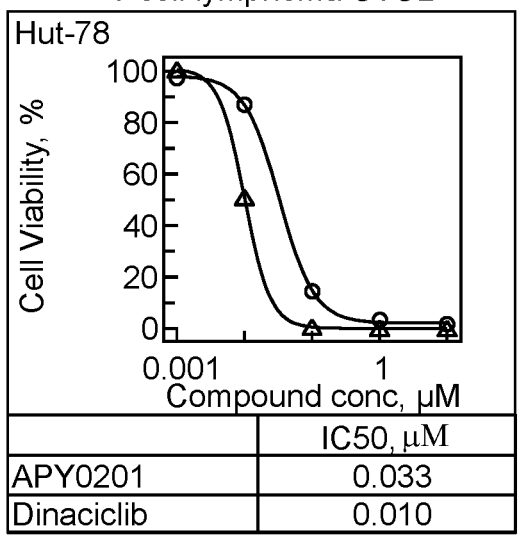
Figure 1D:
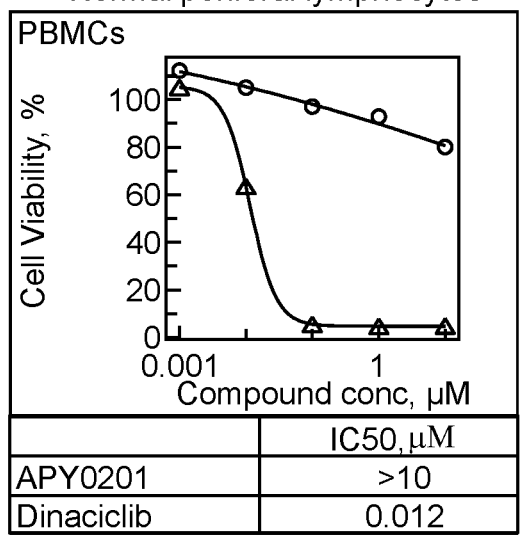

As used in this specification, the singular forms "a," "an," and "the" include plural referents unless the context clearly dictates otherwise.

When a moiety is a cyclic ring, the term "n membered" is used to describe the number of ring atoms a cyclic ring has. For example, a 4 membered cycloalkyl refers to a cycloalkyl having 4 ring atoms, such as cyclobutane.

As used herein, either alone or in combination, the term "alkyl" refers to a straight-chain or branched-chain hydrocarbon containing from 1 to 20 carbon atoms linked exclusively by single bonds and not having any cyclic structure. Examples of alkyl groups includes, without limitation methyl, ethyl, n-propyl, isopropyl, n-butyl, isobutyl, sec-butyl, tert-butyl, pentyl, iso-amyl, hexyl, heptyl, octyl, noyl, decyl, undecyl, dodecyl tridecyl, tetradecyl, pentadecyl, hexadecyl, heptadecyl, octadecyl, nonadecyl, eicosyl, and the like. The term "lower alkyl" refers to a straight-chain or branched-chain hydrocarbon containing from 1 to 6 carbon atoms linked exclusively by single bonds and not having any cyclic structure, such as methyl, ethyl, n-propyl, isopropyl, n-butyl, isobutyl, sec-butyl, tert-butyl, or pentyl.

As used herein, either alone or in combination, the term "aryl" refers to monocyclic, bicyclic (fused), and tricyclic (fused or spiro) hydrocarbon ring system having a total of 5 to 14 ring atoms. When aryl is monocyclic, the monocyclic is aromatic and contains no heteroatom. When aryl is bicyclic or tricyclic, at least one of the ring in the bicyclic or tricyclic is aromatic and contains no heteroatom, and when the other ring(s) is aromatic, the other ring(s) does not contain a heteroatom, but when the other ring(s) is not aromatic, the other ring(s) may or may not contain a heteroatom. The point of attachment can be on any ring atom. Examples of aryl include, without limitation, benzene, naphthalene, indane, 1,2,3,4-tetrahydronaphthalene, chromane, isochromane, 1,2,3,4-tetrahydroquinoline, thiochromane 1,1-dioxide, 6,7,8,9-tetrahydro-5H-benzo[7]annulene, and 2,3-dihydrobenzofuran.

As used herein, either alone or in combination, the term "cycloalkyl" refers to a monocyclic, bicyclic (fused, bridged, or spiro), or tricyclic (fused or spiro) hydrocarbon ring system having a total of three to fourteen ring atoms, which is completely saturated or contains one or more units of unsaturation, but none of the individual ring in the monocyclic, bicyclic, or tricyclic hydrocarbon is aromatic, and none of the ring atoms is a heteroatom. The point of attachment can be on the saturated or unsaturated carbon. A bridged bicyclic cycloalkyl refers to two hydrocarbon rings share three or more carbon atoms, separating the two bridgehead carbon atoms by a bridge containing at least one atom. Examples of cycloalkyl include, but not limited to, cyclopropane, cyclobutane, cyclopentane, cyclohexane, bicyclo[2.2.2]octane, bicyclo[2.2.1]heptane, spiro[2.5]octane, spiro[3.5]nonane, spiro[4.5]decane, and spiro[5.5]undecane.

As used herein, either alone or in combination, the term "heterocyclyl" refers to monocyclic, bicyclic (fused, bridged, or spiro), or tricyclic (fused or spiro) hydrocarbon ring systems having four to fifteen ring atoms, which is completely saturated or contains one or more units of unsaturation, but none of the individual ring in the monocyclic, bicyclic, or tricyclic hydrocarbon is aromatic, and further at least one of the ring atoms is a heteroatom. A bridged bicyclic heterocyclyl is a bridged bicyclic cycloalkyl wherein at least one carbon is replaced with a heteroatom. Examples of heterocyclyl include, but not limited to, azetidine, oxetane, pyrrolidine, piperidine, piperazine, morpholine, and tetrahydrofuran. The point of attachment can be on the saturated or unsaturated carbon or heteroatom.

As used herein, either alone or in combination, the term "heteroaryl" refers to monocyclic, bicyclic (fused), and tricyclic (fused or spiro) ring systems having a total of 5 to 14 ring atoms wherein the monocyclic and at least one of the ring in the bicyclic and tricyclic ring system are aromatic and contain at least one heteroatom selected from S, O, and N. The point of attachment can be on any ring atom. Examples of heteroaryl include, without limitation, furan, thiophene, pyridine, pyrimidine, indole, benzofuran, 4,5,6, 7-tetrahydrobenzofuran, 4,5,6,7-tetrahydrobenzo[b] thiophene, and 4,5,6,7-tetrahydro-1H-indole.

As used herein, either alone or in combination, the term "optionally substituted alkyl" or term to the same effect refers to unsubstituted alkyl (or unsubstituted lower alkyl) or alkyl substituted with one, two, or three groups selected from CN, halo, —NRR, —NHSO$_2$R, —C(O)NRR, —OR, aryl (such as phenyl), cycloalkyl (such as cyclopropane, cyclobutane, cyclopentane, cyclohexane), heterocycloalkyl (such as azetidine, oxetane, pyrrolidine, piperidine, piperazine, morpholine, and tetrahydrofuran), and heteroaryl (such as monocyclic heteroayl), wherein R is independently H, alkyl, aryl (such as phenyl), cycloalkyl (such as cyclopropane, cyclobutane, cyclopentane, cyclohexane), heterocycloalkyl (such as azetidine, oxetane, pyrrolidine, piperidine, piperazine, morpholine, and tetrahydrofuran), or heteroaryl (such as monocyclic heteroaryl). Similarly, the term "optionally substituted lower alkyl" refers to unsubstituted lower alkyl or lower alkyl substituted with one, two, or three groups selected from the same set of groups above.

As used herein, either alone or in combination, the term "optionally substituted aryl" or term to the same effect refers to unsubstituted aryl or aryl substituted with one, two, or three groups selected from alkyl, CN, halo, —NRR, —NHSO$_2$R, —C(O)NRR, —OR, aryl (such as phenyl), cycloalkyl (such as cyclopropane, cyclobutane, cyclopentane, cyclohexane), heterocycloalkyl (such as azetidine, oxetane, pyrrolidine, piperidine, piperazine, morpholine, and tetrahydrofuran), and heteroaryl (such as monocyclic heteroayl), wherein R is independently H, alkyl, aryl (such as phenyl), cycloalkyl (such as cyclopropane, cyclobutane, cyclopentane, cyclohexane), heterocycloalkyl (such as azetidine, oxetane, pyrrolidine, piperidine, piperazine, morpholine, and tetrahydrofuran), or heteroaryl (such as monocyclic heteroaryl). Similarly, the term "optionally substituted phenyl" refers to unsubstituted phenyl or phenyl substituted with one, two, or three groups selected from the same set of groups above.

As used herein, either alone or in combination, the term "optionally substituted heteroaryl" or term to the same effect refers to unsubstituted heteroaryl or heteroaryl substituted with one, two, or three groups selected from alkyl, CN, halo, —NRR, —NHSO$_2$R, —OR, aryl (such as phenyl), cycloalkyl (such as cyclopropane, cyclobutane, cyclopentane, cyclohexane), heterocycloalkyl (such as azetidine, oxetane, pyrrolidine, piperidine, piperazine, morpholine, and tetrahydrofuran), and heteroaryl (such as monocyclic heteroaryl), wherein R is independently H, alkyl, aryl (such as phenyl), cycloalkyl (such as cyclopropane, cyclobutane, cyclopentane, cyclohexane), heterocycloalkyl (such as azetidine, oxetane, pyrrolidine, piperidine, piperazine, morpholine, and tetrahydrofuran), or heteroaryl (such as monocyclic heteroaryl).). Similarly, the term "optionally substituted mono-cyclic heteroaryl" refers to unsubstituted mono-cyclic heteroaryl or mono-cyclic heteroaryl substituted with one, two, or three groups selected from the same set of groups as above.

As used herein, either alone or in combination, the term "optionally substituted cycloalkyl" or term to the same effect refers to unsubstituted cycloalkyl or cycloalkyl substituted with one, two, or three groups selected from alkyl, CN, halo, —NRR, —NHSO$_2$R, —OR, aryl (such as phenyl), cycloalkyl (such as cyclopropane, cyclobutane, cyclopentane, cyclohexane), heterocycloalkyl (such as azetidine, oxetane, pyrrolidine, piperidine, piperazine, morpholine, and tetrahydrofuran), and heteroaryl (such as monocyclic heteroayl), wherein R is independently H, alkyl, aryl (such as phenyl), cycloalkyl (such as cyclopropane, cyclobutane, cyclopentane, cyclohexane), heterocycloalkyl (such as azetidine, oxetane, pyrrolidine, piperidine, piperazine, morpholine, and tetrahydrofuran), or heteroaryl (such as monocyclic heteroaryl.

As used herein, either alone or in combination, the term "optionally substituted heterocyclyl" or term to the same effect refers to unsubstituted heterocycloalkyl or heterocycloalkyl substituted with one, two, or three groups selected from alkyl, CN, halo, —NRR, —NHSO$_2$R, —OR, aryl (such as phenyl), cycloalkyl (such as cyclopropane, cyclobutane, cyclopentane, cyclohexane), heterocycloalkyl (such as azetidine, oxetane, pyrrolidine, piperidine, piperazine, morpholine, and tetrahydrofuran), and heteroaryl (such as monocyclic heteroayl), wherein R is independently H, alkyl, aryl (such as phenyl), cycloalkyl (such as cyclopropane, cyclobutane, cyclopentane, cyclohexane), heterocycloalkyl (such as azetidine, oxetane, pyrrolidine, piperidine, piperazine, morpholine, and tetrahydrofuran), or heteroaryl (such as monocyclic heteroaryl). Similarly, the term "optionally substituted mono-cyclic heterocyclyl" refers to unsubstituted mono-cyclic heterocycyl or mono-cyclic heterocycyl substituted with one, two, or three groups selected from the same set of groups as above.

In the specification, the term "individual" and "mammal" are used interchangeably. Both of them refer to a human or an animal.

The compounds disclosed in the present specification may be present in the form of a pharmaceutically acceptable salt. As used herein, the term "a pharmaceutically acceptable salt" refers to non-toxic acidic/anionic or basic/cationic salt forms of the compounds disclosed in the present specification. Suitable pharmaceutically acceptable salts include acid addition salts which may, e.g., be formed by mixing a solution of the compound disclosed in the present specification with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore when the compounds disclosed in the present specification carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, without limitation, acetate, aspirate, benzenesulfonate, benzoate, besylate, bicarbonate, bisulfate, bitartrate, borate, bromide, calcium, camsylate (or camphorsulphonate), carbonate, chloride, citrate, clavulanate, dihydrochloride, edetate, edisylate, esylate, formate, fumarate, gluceptate, gluconate, glucuronate, glutamate, hexafluorophosphate, hibenzate, hydrabamine, hydrobromide, hydrobromine, hydrochloride, hydroiodide, iodide, isethionate, isothionate, lactate, malate, maleate, malonate, mandelate, mesylate, methylsulfate, nitrate, naphthylate, 2-napsylate, nicotinate, nitrate, oleate, orotate, oxalate, pamoate, palmitate, phosphate/diphosphate/hydrogen phosphate, saccharate, salicylate, stearate, sulfate, succinate, tartrate, tosylate and trifluoroacetate. See Handbook of Pharmaceutical Salts: Properties, Selection, and Use, by Stahl and Wermauth (Wiley-VCH, Weinberg, Germany, 2002).

The compounds disclosed in the present specification may be present in the form of an unsolvated or solvated form. As used herein, the term 'solvate' describes a molecular complex comprising a compound disclosed in the present specification and one or more pharmaceutically acceptable solvent molecules, for example, water, ethanol, DMSO, or other organic solvents. When a compound disclosed in the present specification forms a solvate with water, the term "hydrate" may be used instead of "solvate." Pharmaceutically acceptable solvates include hydrates and solvates wherein the solvent may be isotopically substituted, e.g., D2O, d6-acetone, d6-DMSO.

In a first aspect, the present disclosure is directed to a compound of Formula I or a pharmaceutically acceptable salt thereof:

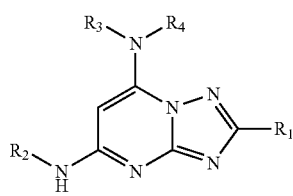

Formula I

Wherein
$R_1$ is optionally substituted alkyl, optionally substituted cycloalkyl, optionally substituted heterocyclyl, optionally substituted aryl, or optionally substituted heteroaryl, provided $R_1$ is not cyclohexyl,
$R_2$ is alkyl, aryl, heteroaryl, —N═CH-alkyl, —N═CH-aryl or —N═CH-heteroaryl, in which each of the alkyl, aryl and heteroaryl is optionally substituted,
$R_3$ and $R_4$ are independently H, optionally substituted alkyl, optionally substituted aryl, optionally substituted heteroaryl, optionally substituted cycloalkyl, or optionally substituted heterocyclyl, provided that when $R_3$ and $R_4$ are such, $R_1$ is not $C_{1-3}$ alkyl; or $R_3$ and $R_4$ together with the nitrogen to which they are attached form an optionally substituted heterocyclyl.

In some embodiments, $R_1$ is optionally substituted phenyl. In some embodiments, $R_1$ is optionally substituted lower alkyl. In some embodiments, $R_1$ is optionally substituted mono-cyclic heteroaryl. In some embodiments, $R_1$ is optionally substituted mono-cyclic heterocyclyl.

In some embodiments, $R_1$ is a phenyl optionally substituted with one or two groups selected from —F, —Cl, —CN, —OH, —C(O)NH$_2$, —CF$_3$, —NH$_2$, —NHSO$_2$-lower alkyl, —OCF$_3$, —O-lower alkyl, and lower alkyl. In some embodiments, $R_1$ is a pyridinyl optionally substituted with one or two groups selected from —F, —Cl, —CN, —OH, —C(O)NH$_2$, —CF$_3$, NH$_2$, —NHSO$_2$-lower alkyl, —OCF$_3$, —O-lower alkyl, and lower alkyl. In some embodiments, $R_1$ is a pyrimidinyl optionally substituted with one or two groups selected from —F, —Cl, —CN, —OH, —C(O)NH$_2$, —CF$_3$, —NH$_2$, —NHSO$_2$-lower alkyl, —OCF$_3$, —O-lower alkyl, and lower alkyl. In some embodiments, $R_1$ is quinolinyl or isoquinolinyl optionally substituted with one or two groups selected from —F, —Cl, —CN, —OH, —C(O)NH$_2$, —CF$_3$, —NH$_2$, —NHSO$_2$-lower alkyl, —OCF$_3$, —O-lower alkyl, and lower alkyl.

In some embodiments, $R_1$ is a lower alkyl optionally substituted with one or two groups selected from —F, —Cl, —CN, —OH, —C(O)NH$_2$, —CF$_3$, —NH$_2$, —OCF$_3$, —O-lower alkyl, lower alkyl, phenyl, and mono-cyclic heteroaryl. In some embodiments, $R_1$ is azetidinyl, oxetanyl, tetrahydrofuran, or pyrrolidinyl, each of which is optionally substituted with one or two groups selected from —F, —Cl, —CN, —OH, —C(O)NH$_2$, —CF$_3$, —NH$_2$, —OCF$_3$, —O-lower alkyl, and lower alkyl.

In some embodiments, $R_2$ is —N═CH-aryl, —N═CH-heteroaryl, or —N═CH-alkyl, each of aryl, heteroaryl, and alkyl is optionally substituted with one or two groups selected from —F, —Cl, —CN, —OH, —C(O)NH$_2$, —CF$_3$, —NH$_2$, —NHSO$_2$-lower alkyl, —OCF$_3$, —O-lower alkyl, lower alkyl, phenyl, and mono-cyclic heteroaryl. In some embodiments, $R_2$ is —N═CH-phenyl, —N═CH-naphthalenyl, —N═CH-pyridinyl, —N═CH-indolyl, or —N═CH-lower alkyl, each of phenyl, naphthalenyl, pyridinyl, indolyl and lower alkyl is optionally substituted with one or two groups selected from —F, —Cl, —CN, —OH, —C(O)NH$_2$, —CF$_3$, —NH$_2$, —NHSO$_2$-lower alkyl, —OCF$_3$, —O-lower alkyl, lower alkyl, phenyl, and mono-cyclic heteroaryl.

In some embodiments, $R_3$ and $R_4$ are independently lower alkyl optionally substituted with one or two groups selected from CF$_3$, OH, CN, NH$_2$, —OCF$_3$, and —O-lower alkyl. In some embodiments, $R_3$ and $R_4$ together with the nitrogen to which they are attached form a mono or bi-cyclic heterocyclyl or a bi-cyclic aryl, each of the mono, bi-cyclic heterocyclyl and bi-cyclic aryl is optionally substituted with one or two groups selected from lower alkyl. The mono or bi-cyclic heterocyclyl or a bi-cyclic aryl may comprise additional heteroatom(s) selected from N, O, and S, In some embodiments, the mono-cyclic heterocyclyl is a 4, 5, 6, or 7 membered heterocyclyl. Examples of the mono-cyclic heterocyclyl include aziridine, azetidine, pyrolidine, piperidine, morpholine, piperazine, thiomorpholine, thiomorpholine-S-oxide, thiomorpholine-S,S-dioxide, azepane, 1,4-oxazepane, and 1,4-thiazepane.

In some embodiments, $R_1$ is

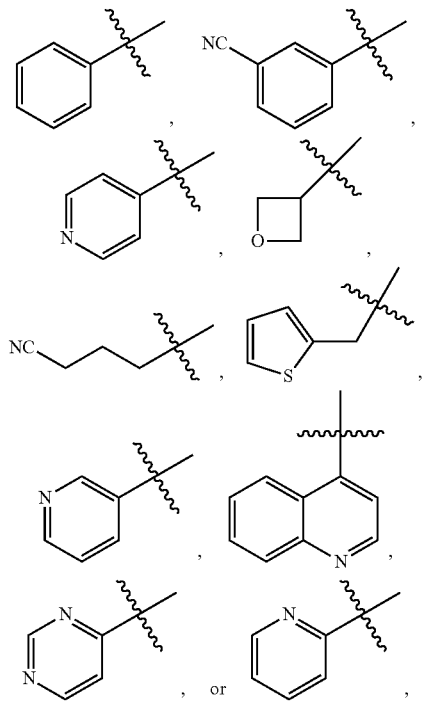

, or , wherein ⌇ indicates the point of attachment to the remaining moiety of the molecule.

In some embodiments, $R_2$ is

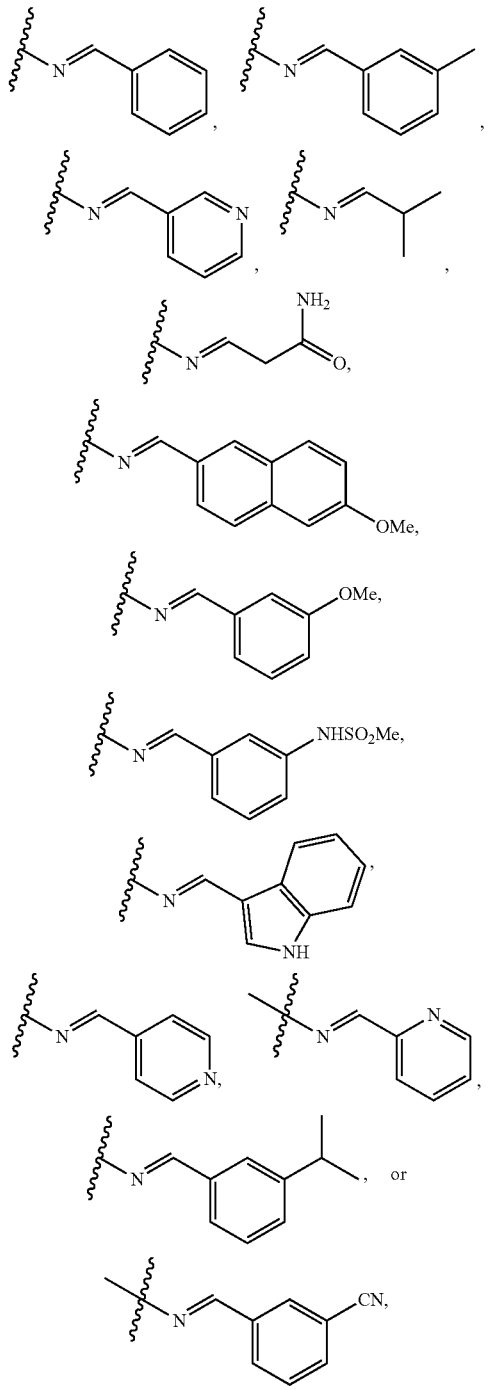

wherein ⌇ indicates the point of attachment to the remaining moiety of the molecule.

In some embodiments, $R_3$ and $R_4$ are independently methyl, isopropyl, or 2-hydroxyl ethyl. In some embodiments, $R_3$ and $R_4$ together with the nitrogen to which they are attached form one of the following rings:

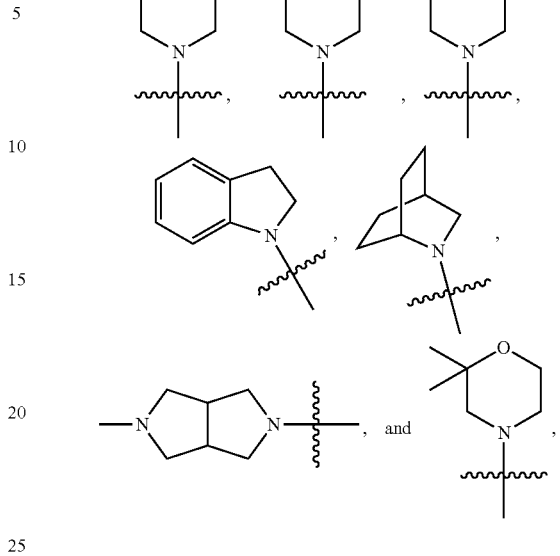

wherein ⌇ indicates the point of attachment to the remaining moiety of the molecule.

In some embodiments, the compound of Formula I and/or a pharmaceutically acceptable salt thereof is a compound of Formula II and/or a pharmaceutically acceptable salt thereof:

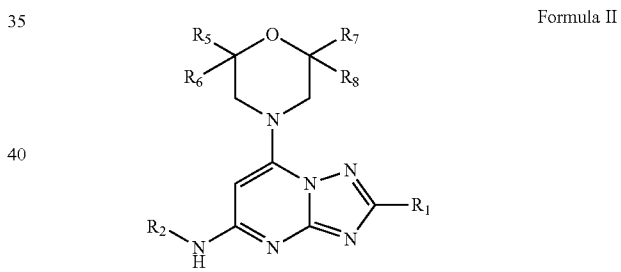

Formula II

Wherein $R_1$ is optionally substituted alkyl, optionally substituted cycloalkyl, optionally substituted heterocyclyl, optionally substituted aryl, or optionally substituted heteroaryl, provided $R_1$ is not cyclohexyl, $R_2$ is optionally substituted alkyl, optionally substituted aryl, optionally substituted heteroaryl, N=CH-alkyl, N=CH-aryl or N=CH-heteroaryl in which alkyl, aryl and heteroaryl can be optionally substituted, $R_5$, $R_6$, $R_7$, and $R_8$ are independently H or methyl.

In some embodiments of Formula II, $R_1$ is optionally substituted phenyl. In some embodiments of Formula II, $R_1$ is optionally substituted lower alkyl. In some embodiments of Formula II, $R_1$ is optionally substituted mono-cyclic heteroaryl. In some embodiments of Formula II, $R_1$ is optionally substituted mono-cyclic heterocyclyl.

In some embodiments of Formula II, $R_1$ is a phenyl optionally substituted with one or two groups selected from —F, —Cl, —CN, —OH, —C(O)NH$_2$, —CF$_3$, —NH$_2$, —NHSO$_2$-lower alkyl, —OCF$_3$, —O-lower alkyl, and lower alkyl. In some embodiments of Formula II, $R_1$ is a pyridinyl optionally substituted with one or two groups selected from —F, —Cl, —CN, —OH, —C(O)NH₂, —CF₃, NH₂, —NHSO₂-lower alkyl, —OCF₃, —O-lower alkyl, and lower alkyl. In some embodiments of Formula II, R₁ is a pyrimidinyl optionally substituted with one or two groups selected from —F, —Cl, —CN, —OH, —C(O)NH₂, —CF₃, —NH₂, —NHSO₂-lower alkyl, —OCF₃, —O-lower alkyl, and lower alkyl. In some embodiments of Formula II, R₁ is quinolinyl or isoquinolinyl optionally substituted with one or two groups selected from —F, —Cl, —CN, —OH, —C(O)NH₂, —CF₃, —NH₂, —NHSO₂-lower alkyl, —OCF₃, —O-lower alkyl, and lower alkyl.

In some embodiments of Formula II, R₁ is a lower alkyl optionally substituted with one or two groups selected from —F, —Cl, —CN, —OH, —C(O)NH₂, —CF₃, —NH₂, —OCF₃, —O-lower alkyl, lower alkyl, phenyl, and mono-cyclic heteroaryl. In some embodiments of Formula II, R₁ is azetidinyl, oxetanyl, tetrahydrofuran, or pyrrolidinyl, each of which is optionally substituted with one or two groups selected from —F, —Cl, —CN, —OH, —C(O)NH₂, —CF₃, —NH₂, —OCF₃, —O-lower alkyl, and lower alkyl.

In some embodiments of Formula II, R₂ is —N=CH-aryl, —N=CH-heteroaryl, or —N=CH-alkyl, each of aryl, heteroaryl, and alkyl is optionally substituted with one or two groups selected from —F, —Cl, —CN, —OH, —C(O)NH₂, —CF₃, —NH₂, —NHSO₂-lower alkyl, —OCF₃, —O-lower alkyl, lower alkyl, phenyl, and mono-cyclic heteroaryl. In some embodiments of Formula II, R₂ is —N=CH-phenyl, —N=CH-naphthalenyl, —N=CH-pyridinyl, —N=CH-indolyl, or —N=CH-lower alkyl, each of phenyl, naphthalenyl, pyridinyl, indolyl, and lower alkyl is optionally substituted with one or two groups selected from —F, —Cl, —CN, —OH, —C(O)NH₂, —CF₃, —NH₂, —NHSO₂-lower alkyl, —OCF₃, —O-lower alkyl, lower alkyl, phenyl, and mono-cyclic heteroaryl.

In some embodiments of Formula II, R₁ is

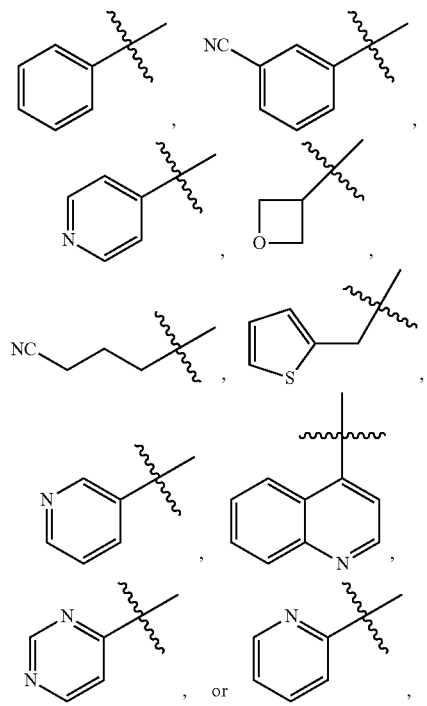

wherein ⌇ indicates the point of attachment to the remaining moiety of the molecule.

In some embodiments of Formula II, R₂ is

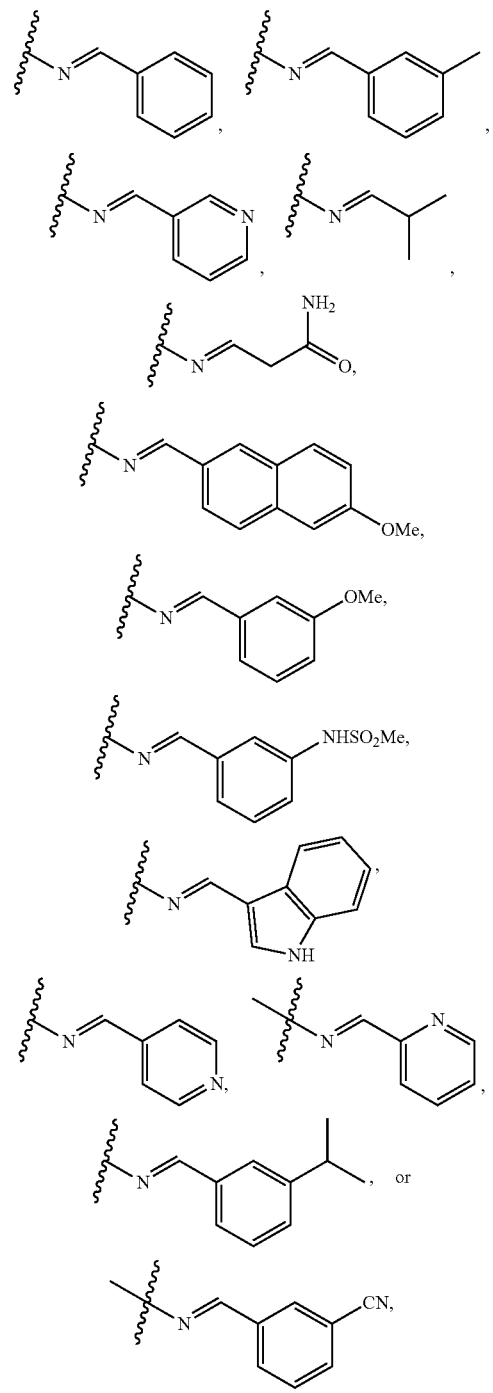

wherein ⌇ indicates the point of attachment to the remaining moiety of the molecule.

In some embodiments, the compound of Formula I and/or a pharmaceutically acceptable salt thereof is a compound of Formula III and/or a pharmaceutically acceptable salt thereof:

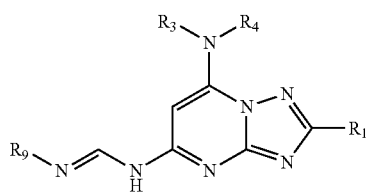

Formula III

Wherein
R₁ is optionally substituted alkyl, optionally substituted cycloalkyl, optionally substituted heterocyclyl, optionally substituted aryl, or optionally substituted heteroaryl, provided R₁ is not cyclohexyl, R₉ is optionally substituted alkyl, optionally substituted aryl, or optionally substituted heteroaryl, R₃ and R₄ are independently H, optionally substituted alkyl, optionally substituted aryl, optionally substituted heteroaryl, optionally substituted cycloalkyl, or optionally substituted heterocyclyl; or R₃ and R₄ together with the nitrogen to which they are attached form an optionally substituted heterocyclyl.

In some embodiments of Formula III, R₁ is optionally substituted phenyl. In some embodiments, R₁ is optionally substituted lower alkyl. In some embodiments of Formula III, R₁ is optionally substituted mono-cyclic heteroaryl. In some embodiments of Formula III, R₁ is optionally substituted mono-cyclic heterocyclyl.

In some embodiments of Formula III, R₁ is a phenyl optionally substituted with one or two groups selected from —F, —Cl, —CN, —OH, —C(O)NH₂, —CF₃, —NH₂, —NHSO₂-lower alkyl, —OCF₃, —O-lower alkyl, and lower alkyl. In some embodiments of Formula III, R₁ is a pyridinyl optionally substituted with one or two groups selected from —F, —Cl, —CN, —OH, —C(O)NH₂, —CF₃, NH₂, —NHSO₂-lower alkyl, —OCF₃, —O-lower alkyl, and lower alkyl. In some embodiments of Formula III, R₁ is a pyrimidinyl optionally substituted with one or two groups selected from —F, —Cl, —CN, —OH, —C(O)NH₂, —CF₃, —NH₂, —NHSO₂-lower alkyl, —OCF₃, —O-lower alkyl, and lower alkyl. In some embodiments of Formula III, R₁ is quinolinyl or isoquinolinyl optionally substituted with one or two groups selected from —F, —Cl, —CN, —OH, —C(O)NH₂, —CF₃, —NH₂, —NHSO₂-lower alkyl, —OCF₃, —O-lower alkyl, and lower alkyl.

In some embodiments of Formula III, R₁ is a lower alkyl optionally substituted with one or two groups selected from —F, —Cl, —CN, —OH, —C(O)NH₂, —CF₃, —NH₂, —OCF₃, —O-lower alkyl, lower alkyl, phenyl, and mono-cyclic heteroaryl. In some embodiments of Formula III, R₁ is azetidinyl, oxetanyl, tetrahydrofuran, or pyrrolidinyl, each of which is optionally substituted with one or two groups selected from —F, —Cl, —CN, —OH, —C(O)NH₂, —CF₃, —NH₂, —OCF₃, —O-lower alkyl, and lower alkyl.

In some embodiments of Formula III, R₉ is aryl, heteroaryl, or alkyl each of which is optionally substituted with one or two groups selected from —F, —Cl, —CN, —OH, —C(O)NH₂, —CF₃, —NH₂, —NHSO₂-lower alkyl, —OCF₃, —O-lower alkyl, lower alkyl, phenyl, and mono-cyclic heteroaryl. In some embodiments of Formula III, R₉ is phenyl, naphthalenyl, pyridinyl, indolyl, or lower alkyl, each of phenyl, naphthalenyl, pyridinyl, indolyl and lower-alkyl is optionally substituted with one or two groups selected from —F, —Cl, —CN, —OH, —C(O)NH₂, —CF₃, —NH₂, —NHSO₂-lower alkyl, —OCF₃, —O-lower alkyl, lower alkyl, phenyl, and mono-cyclic heteroaryl.

In some embodiments of Formula III, R₃ and R₄ are independently lower alkyl optionally substituted with one or two groups selected from CF₃, OH, CN, NH₂, —OCF₃, and —O-lower alkyl. In some embodiments of Formula III, R₃ and R₄ together with the nitrogen to which they are attached form a mono or bi-cyclic heterocyclyl or a bi-cyclic aryl, each of the mono, bi-cyclic heterocyclyl and bi-cyclic aryl is optionally substituted with one or two groups selected from lower alkyl. The mono or bi-cyclic heterocyclyl or a bi-cyclic aryl may comprise additional heteroatom(s) selected from N, O, and S, In some embodiments of Formula III, the mono-cyclic heterocyclyl is a 4, 5, 6, or 7 membered heterocyclyl. Examples of the mono-cyclic heterocyclyl include aziridine, azetidine, pyrolidine, piperidine, morpholine, piperazine, thiomorpholine, thiomorpholine-S-oxide, thiomorpholine-S,S-dioxide, azepane, 1,4-oxazepane, and 1,4-thiazepane.

In some embodiments of Formula III, R₁ is

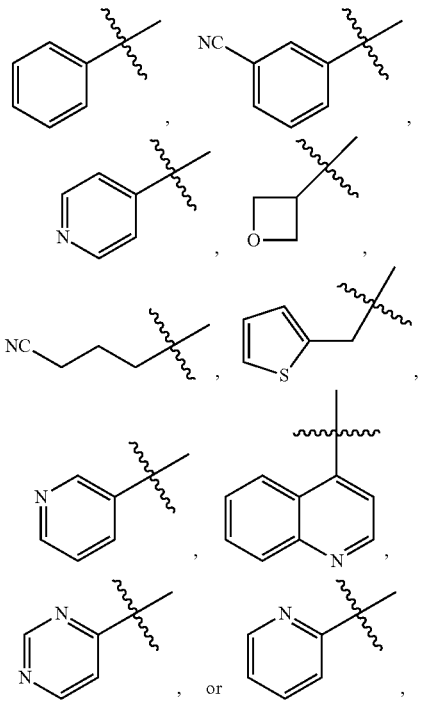

wherein ⌇ indicates the point of attachment to the remaining moiety of the molecule.

In some embodiments of Formula III, R₂ is

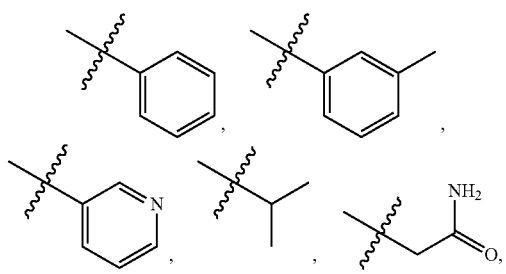

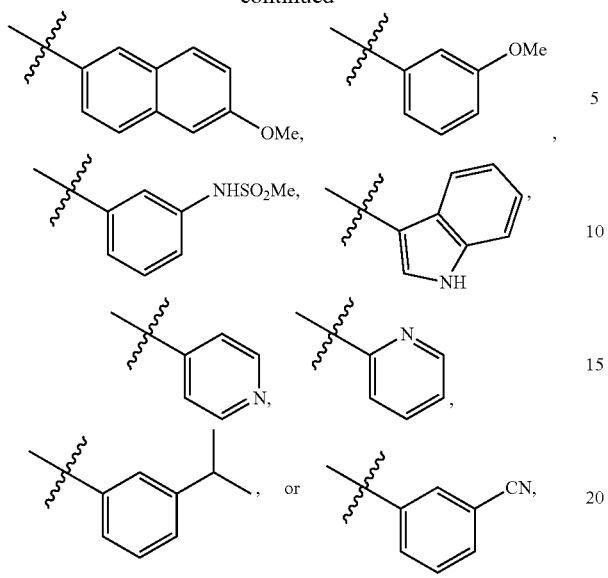

wherein ⌇ indicates the point of attachment to the remaining moiety of the molecule.

In some embodiments of Formula III, $R_3$ and $R_4$ are independently methyl, isopropyl, or 2-hydroxyl ethyl. In some embodiments, $R_3$ and $R_4$ together with the nitrogen to which they are attached form one of the following rings:

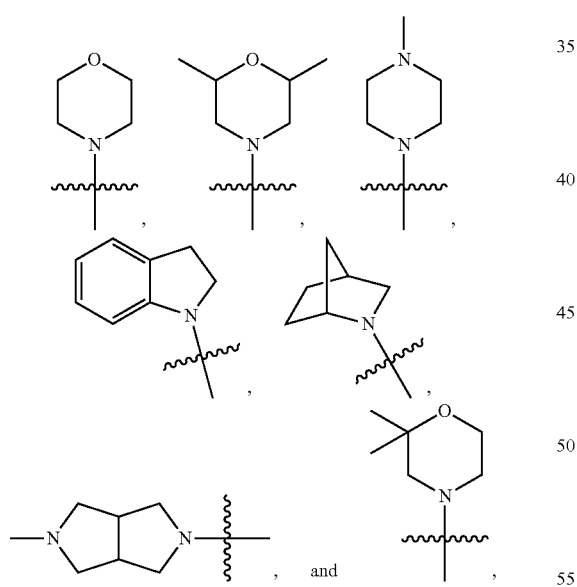

wherein ⌇ indicates the point of attachment to the remaining moiety of the molecule.

It is within the scope of the present disclosure that each embodiment for each of $R_1$-$R_9$, as disclosed herein, can be in any combination with one another, unless otherwise provided for.

In some embodiments, the compound of Formula I and/or a pharmaceutically acceptable salt thereof is selected from the following compounds:

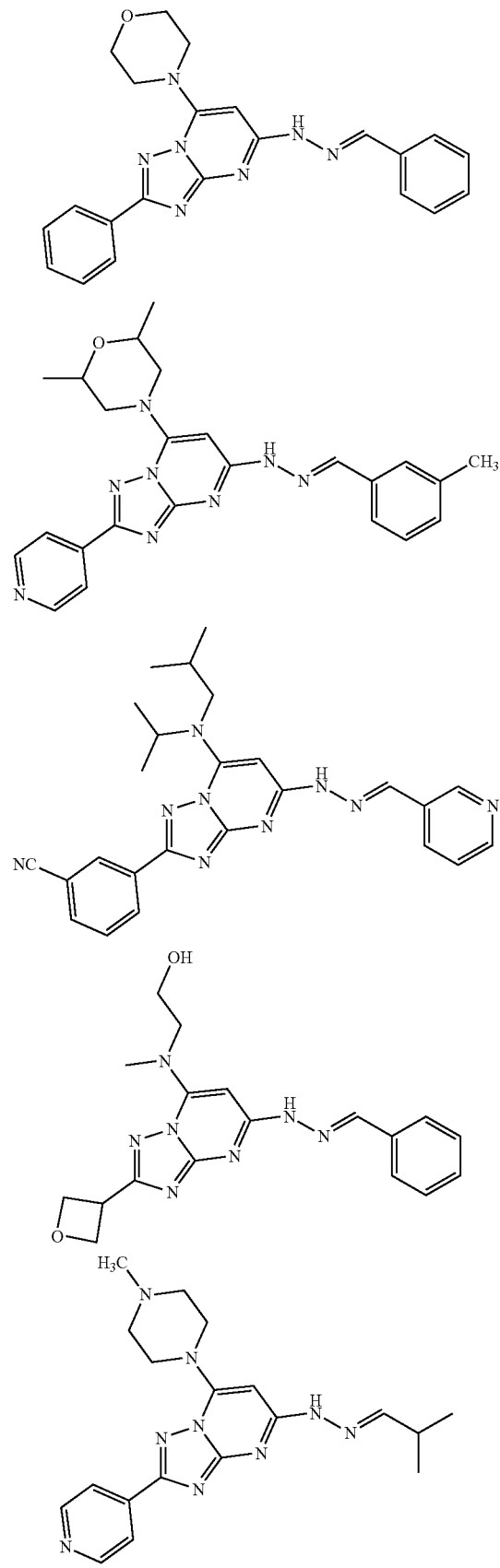

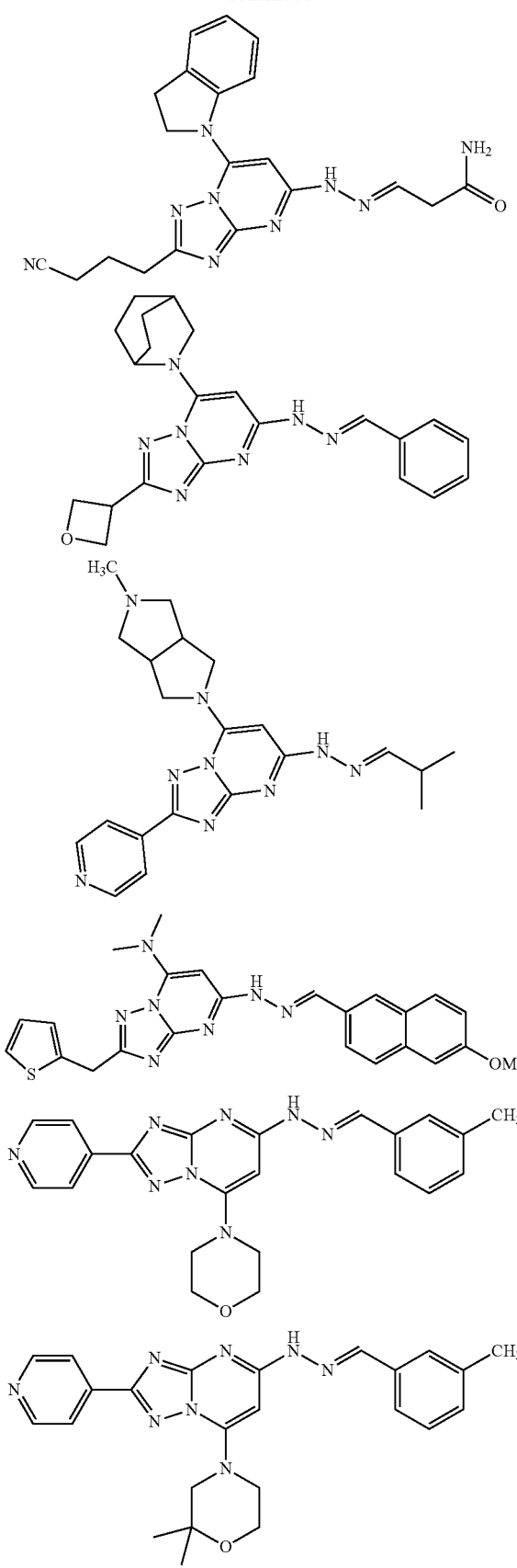
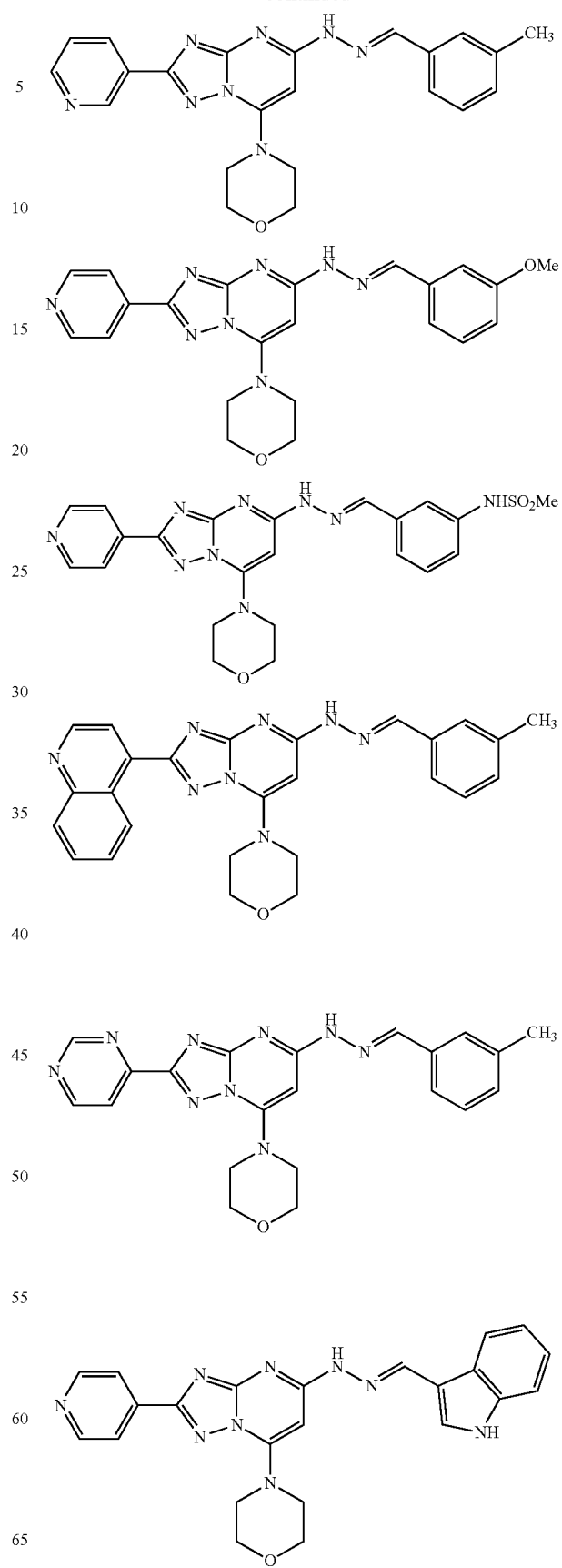

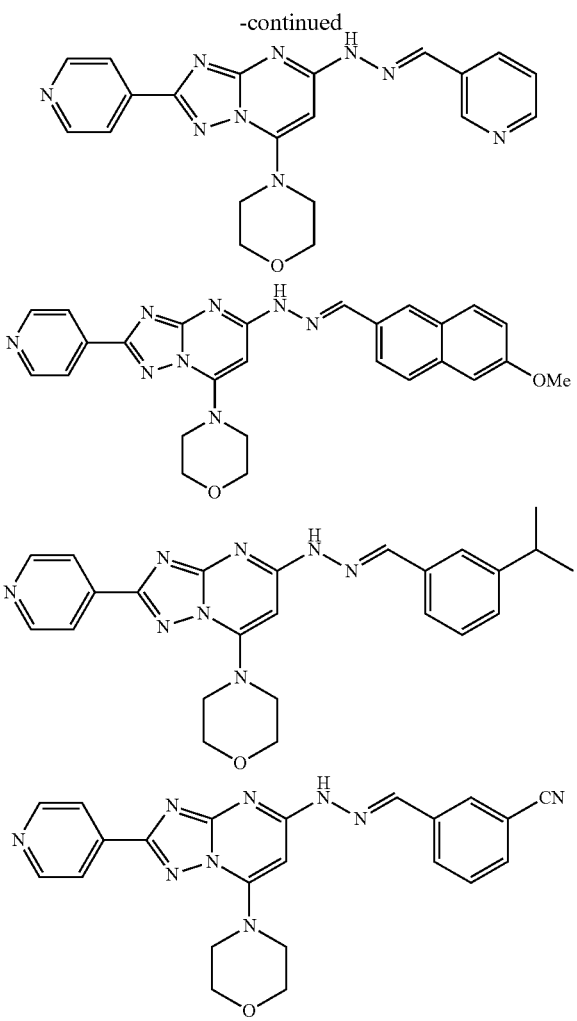

In a second aspect, the present disclosure is directed to a pharmaceutical composition comprising a compound of Formula I and/or a pharmaceutically acceptable salt thereof, including each embodiments thereof, disclosed in the present specification. The pharmaceutical composition may be administered to an individual alone, or in combination with other therapeutically active compounds, agents, drugs or hormones. In addition to the compound of Formula I and/or a pharmaceutically acceptable salt thereof, including each embodiments thereof, as disclosed in the present specification, the pharmaceutical composition may comprise another therapeutically effective agent known to treat cancers or auto-immune diseases.

The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

The pharmaceutical composition may be provided in the form of tablets or capsules for oral administration, containing about 1.0 to about 1000 milligrams of the compound of Formula I and/or a pharmaceutically acceptable salt thereof (including each embodiment thereof), such as about 1.0, 5.0, 10, 15, 20, 25, 50, 75, 100, 150, 200, 250, 300, 400, 500, 600, 750, 800, 900, and 1000 milligrams of the compound of Formula I and/or a pharmaceutically acceptable salt thereof (including each embodiment thereof).

The pharmaceutical composition can further comprise a pharmaceutically acceptable carrier. As used herein, the term "pharmaceutically acceptable carrier" refers to any carrier that has substantially no long term or permanent detrimental effect when administered and encompasses terms such as "pharmaceutically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent.

Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmaceutically acceptable carrier can depend on the mode of administration. Except insofar as any pharmaceutically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); Remington: The Science and Practice of Pharmacy (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine and any modifications are well within the scope of one skilled in the art and from the teaching herein.

In a third aspect, the present disclosure is directed to a method of treating an individual suffering from a disease treatable by inhibition of PIKfyve kinase, which method comprises administering to the individual in need thereof a therapeutically effective amount of the pharmaceutical composition comprising a compound of Formula I and/or a pharmaceutically acceptable salt thereof (including each embodiment thereof), wherein such administration reduces or eliminates a symptom associated with the disease.

The disease includes various forms of cancers and auto-immune disorders. For example, cancer include multiple myeloma, non-hodgkins' lymphoma, T-cell lymphoma, and acute myelomonocytic leukemia. Autoimmune disorders include, for example, rheumatoid arthritis, inflammatory bowel diseases, psoriasis, and multiple sclerosis.

The following examples are illustrative in nature and are in no way intended to be limiting.

EXAMPLES

Example 1

The compound of Formula I can be prepared by methods known to those skilled in the art as illustrated below.

The reaction of a carboxylic acid with aminoguanidine at high temperature under acidic conditions forms a 3-substituted-1H-1,2,4-triazol-5-amine:

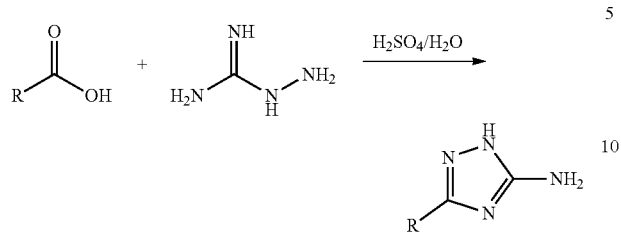

For example, benzoic acid reacts with aminoguanidine (Kurzer, F.; Godfrey, L. E. A. Angewandte Chemie 75, (23) 1157-75 (1963)) to afford 3-phenyl-1H-1,2,4-triazol-5-amine:

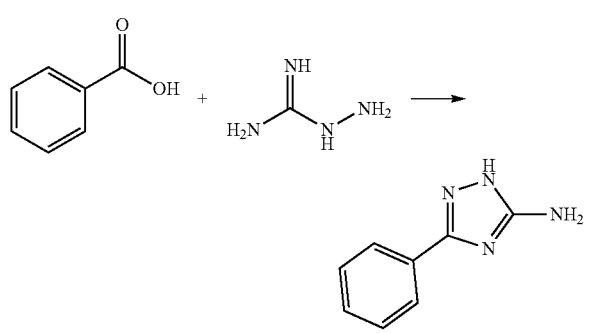

Such aminotriazoles will react with malonic acid esters or halides under a variety of conditions in such a way as to form 2-substituted-[1,2,4]triazolo[1,5-a]pyrimidine-5,7-diols (Bioorganic & Medicinal Chemistry Letters 22, (9), 3198-3202 (2012)):

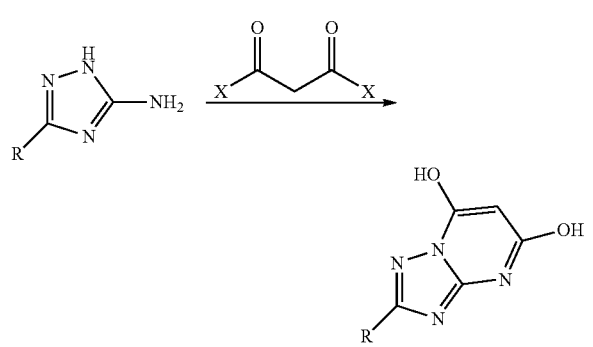

Thus 3-phenyl-1H-1,2,4-triazol-5-amine reacts with malonoyl chloride to form 2-phenyl-[1,2,4]triazolo[1,5-a]pyrimidine-5,7-diol:

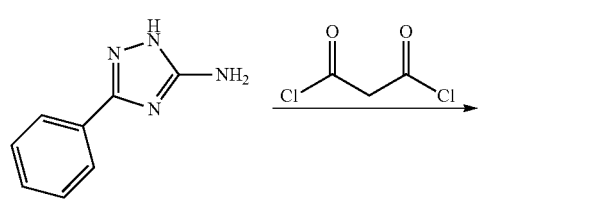

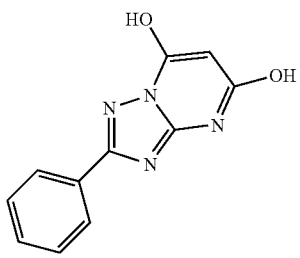

The two hydroxy groups can be readily replaced by chlorines or other halogens using any of a number of halogenating agents such as phosphorus oxychloride, $PBr_5$, thionyl chloride or oxalyl chloride (Bioorganic & Medicinal Chemistry Letters 22, (9), 3198-3202 (2012)).

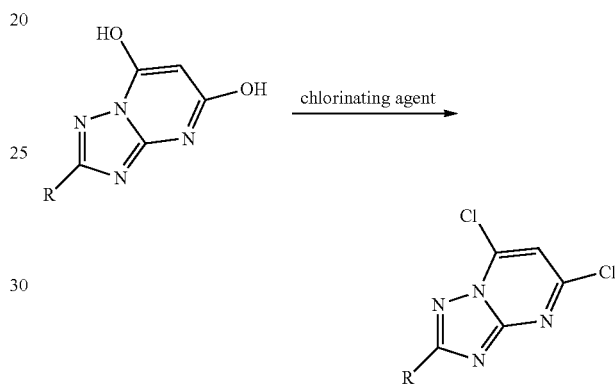

Thus 2-phenyl-[1,2,4]triazolo[1,5-a]pyrimidine-5,7-diol readily reacts with phosphorus oxychloride to afford 5,7-dichloro-2-phenyl-[1,2,4]triazolo[1,5-a]pyrimidine:

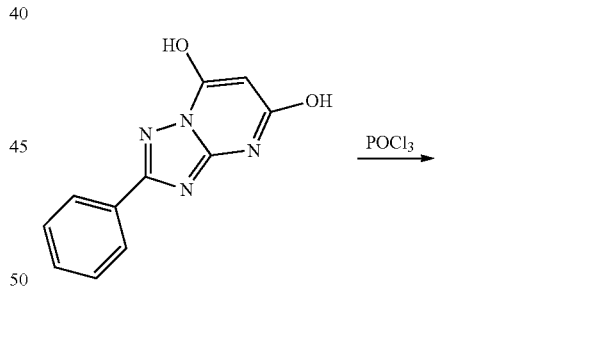

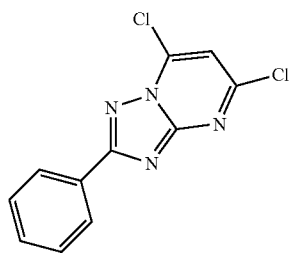

The 7-Cl group is selectively replaced under mild conditions with a secondary amine (U.S. Pat. No. 8,957,064 B2):

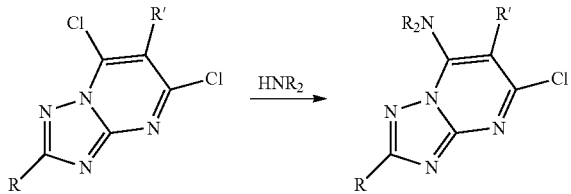

Thus 5,7-dichloro-2-phenyl-[1,2,4]triazolo[1,5-a]pyrimidine reacts with morpholine to afford 4-(5-chloro-2-phenyl-[1,2,4]triazolo[1,5-a]pyrimidin-7-yl)morpholine:

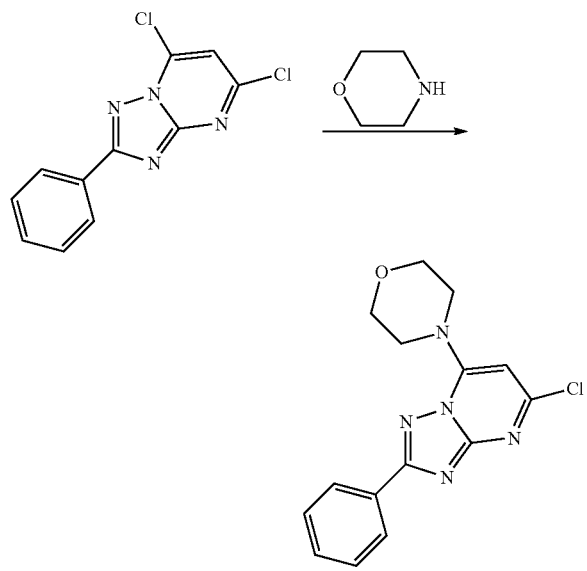

The 5-chloro group may then be displaced under harsher conditions with a strongly nucleophilic amine such as ammonia, methyl amine or hydrazine as follows (JP 04099775 A (1992)):

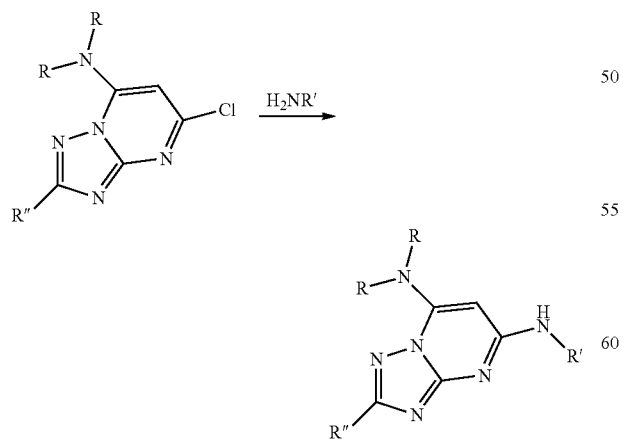

Thus 4-(5-chloro-2-phenyl-[1,2,4]triazolo[1,5-a]pyrimidin-7-yl)morpholine reacts at high temperature with hydrazine hydrate to provide 4-(5-hydrazinyl-2-phenyl-[1,2,4]triazolo[1,5-a]pyrimidin-7-yl)morpholine:

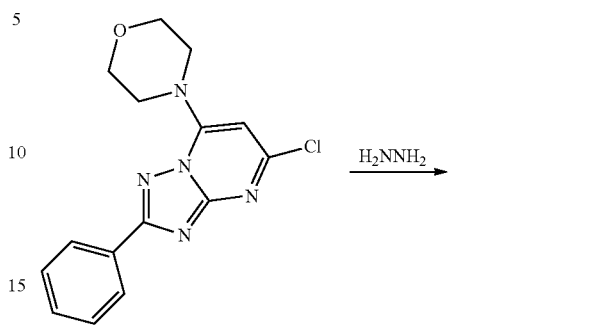

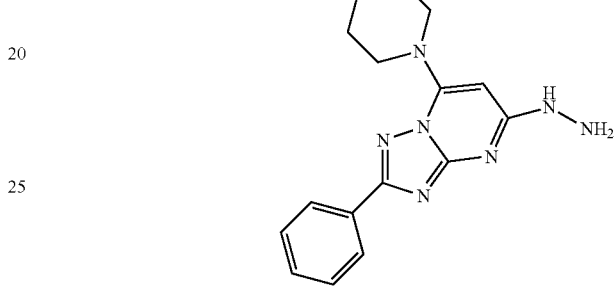

If the amine which displaces the 5-chloro group is hydrazine, it may be reacted with most common aldehydes to form the corresponding imino compound:

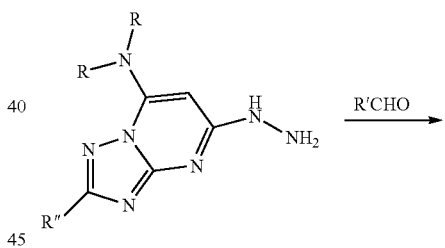

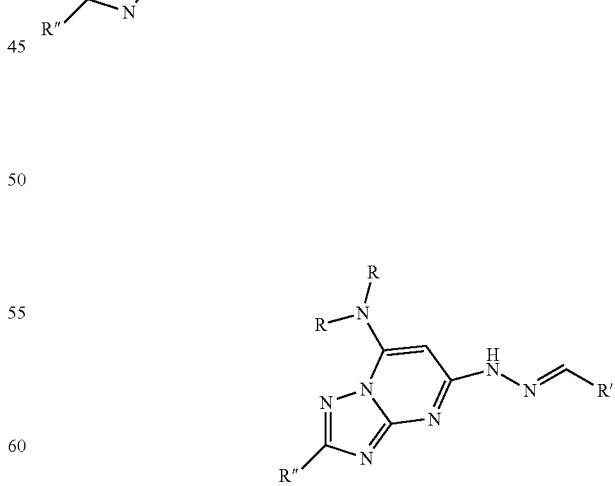

Thus 4-(5-hydrazinyl-2-phenyl-[1,2,4]triazolo[1,5-a]pyrimidin-7-yl)morpholine reacts with an aldehyde such as benzaldehyde to afford (E)-4-(5-(2-benzylidenehydrazinyl)-2-phenyl-[1,2,4]triazolo[1,5-a]pyrimidin-7-yl)morpholine:

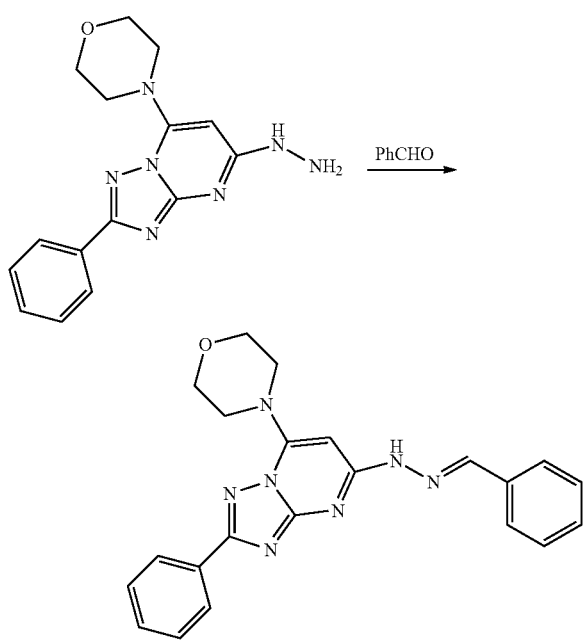

Example 2

Preparation of (E)-4-(5-(2-(3-methylbenzylidene)hydrazinyl)-2-(pyridin-4-yl)-[1,2,4]triazolo[1,5-a]pyrimidin-7-yl)morpholine (Compound 1)

Step 1: Preparation of 3-(pyridin-4-yl)-1H-1,2,4-triazol-5-amine

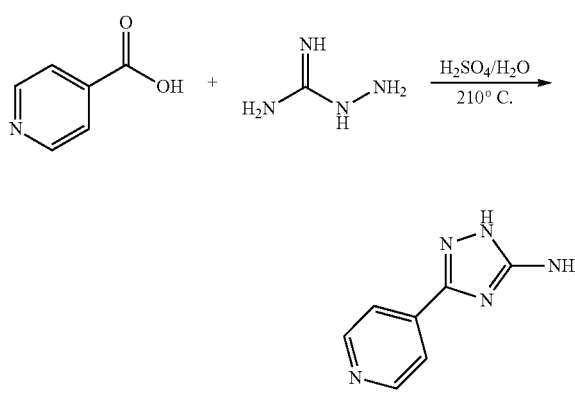

An intimate mixture of isonicotinic acid (13.36 g, 108.5 mmol) and aminoguanidine hydrochloride (5.0 g, 45.2 mmol) in an open vial was heated at 230° C. for 1 h at which time gas evolution had ceased. The cooled residue was in water and purified by chromatography on Amberlite CG-50—type 1 resin. Elution with water removed the excess isonicotinic acid and further elution with 0.5 M ammonium carbonate solution afforded pure 3-(pyridin-4-yl)-1H-1,2,4-triazol-5-amine (5.97 g, 82% yield). [M+H]$^+$=161.8.

Step 2: Preparation of 5,7-dichloro-2-(pyridin-4-yl)-[1,2,4]triazolo[1,5-a]pyrimidine

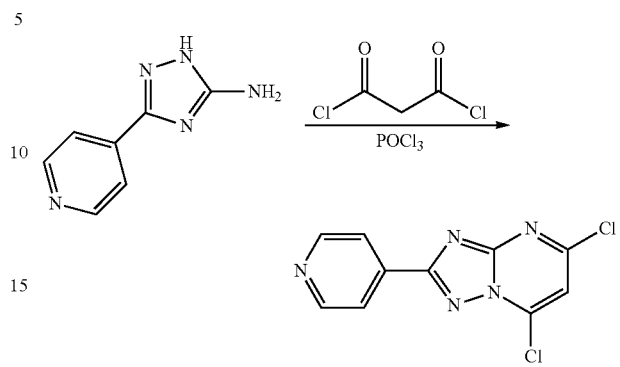

3-(Pyridin-4-yl)-1H-1,2,4-triazol-5-amine (5.0 g, 31.0 mmol) was dissolved in acetonitrile (125 mL) and treated with malonyl chloride (4.37 g, 31.0 mmol) and stirred under an inert atmosphere for 2.5 h at which time another portion of malonyl chloride (2.18 g, 15 mmol). After stirring an additional 2 h the reaction mixture was partitioned between water and ethyl acetate. The layers were separated and the aqueous layer extracted a second time. The combined layers were dried and evaporated to dryness to afford a crude residue which was suspended in ice cooled phosphorus oxychloride (50 mL). The mixture was heated at reflux for 5 h. The reaction mixture was cooled and the majority of the solvent removed under reduced pressure. The residue was partitioned between dichloromethane and water, the organic layer dried and evaporated to leave a residue. Purification of the crude product by Combi-flash chromatography using ethyl acetate-hexane afforded pure 5,7-dichloro-2-(pyridin-4-yl)-[1,2,4]triazole[1,5-a]pyrimidine (0.760 g, 9.2% yield). [M+H]$^+$=265.9.

Step 3: Preparation of 4-(5-chloro-2-(pyridin-4-yl)-[1,2,4]triazolo[1,5-a]pyrimidin-7-yl)morpholine

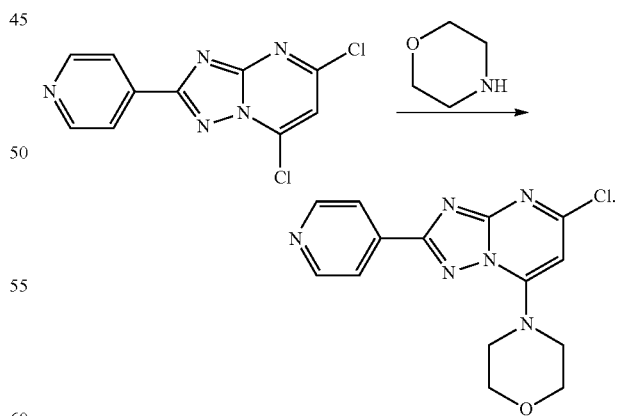

5,7-dichloro-2-(pyridin-4-yl)-[1,2,4]triazole[1,5-a]pyrimidine (0.520 g, 1.95 mmol) was dissolved in dioxane (10 mL) and treated with morpholine (0.340 g, 3.9 mmol). The reaction mixture was stirred at room temperature for 30 min at which time the mixture was partitioned between dichloromethane and water. The layers were separated and the aqueous layer re-extracted with dichloromethane. The combined organic layers were dried and evaporated to dryness. The solid residue was triturated with a little methanol, filtered and dried to afford pure 4-(5-chloro-2-(pyridin-4-yl)-[1,2,4]triazolo[1,5-a]pyrimidin-7-yl)morpholine (0.600 g, 97% yield). [M+H]$^+$=316.8.

Step 4: Preparation of ((E)-4-(5-(2-(3-methylbenzylidene)hydrazinyl)-2-(pyridin-4-yl)-[1,2,4]triazolo[1,5-a]pyrimidin-7-yl)morpholine (Compound 1)

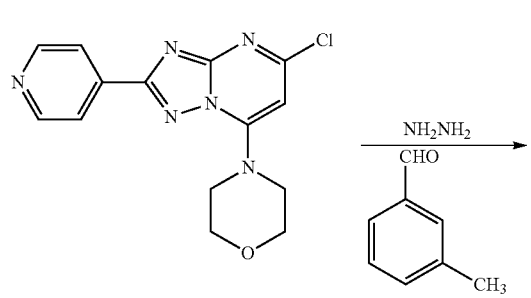

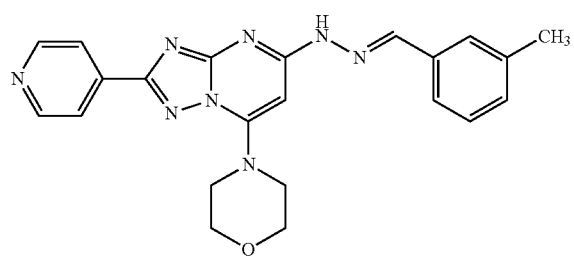

1

4-(5-chloro-2-(pyridin-4-yl)-[1,2,4]triazolo[1,5-a]pyrimidin-7-yl)morpholine (0.600 g, 1.9 mmol) and hydrazine hydrate (1 mL) were suspended in ethanol (25 mL) in a sealed vial and heated at 150° C. in a microwave reactor for 10 min, followed by 120° C. for a further 10 min. The cooled reaction mixture was partitioned between water and ethyl acetate. The aqueous phase was extracted a second time with ethyl acetate and the combined organic extracts were dried and evaporated to dryness. The crude residue ([M+H]$^+$=313.1) was suspended in methanol (10 mL) and acetic acid (10 μL) and 3-methylbenzaldehyde (0.228 g, 1.9 mmol) were added. The resulting mixture was stirred at room temperature for 30 min at which time additional methanol (5 mL) and 3-methylbenzaldehyde (0.114 g) were added. After a further 60 min stirring at room temperature, the reaction was filtered and the solid thus obtained (0.597 g, 76% yield) was taken up in pyridine and further purified by HPLC to afford pure ((E)-4-(5-(2-(3-methylbenzylidene)hydrazinyl)-2-(pyridin-4-yl)-[1,2,4]triazolo[1,5-a]pyrimidin-7-yl)morpholine (Compound 1) [M+H]$^+$=415.1.

Example 3

Preparation of (E)-2,2-dimethyl-4-(5-(2-(3-methylbenzylidene)hydrazinyl)-2-(pyridin-4-yl)-[1,2,4]triazolo[1,5-a]pyrimidin-7-yl)morpholine (Compound 2)

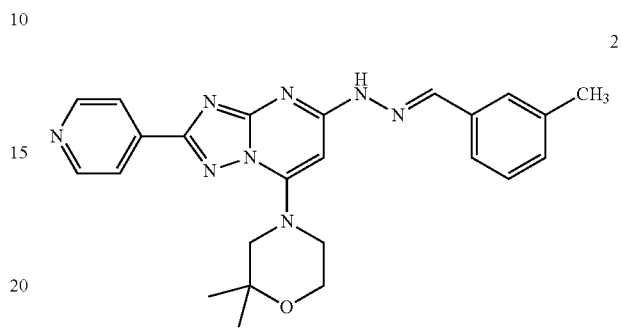

2

Using the procedures described in Example 2, substituting 2,2-dimethylmorpholine for morpholine in step 3, (E)-2,2-dimethyl-4-(5-(2-(3-methylbenzylidene)hydrazinyl)-2-(pyridin-4-yl)-[1,2,4]triazolo[1,5-a]pyrimidin-7-yl)morpholine is prepared. [M+H]$^+$=443.1.

Example 4

Preparation of (E)-4-(5-(2-(3-methylbenzylidene)hydrazinyl)-2-(pyridin-3-yl)-[1,2,4]triazole[1,5-a]pyrimidin-7-yl)morpholine (Compound 3)

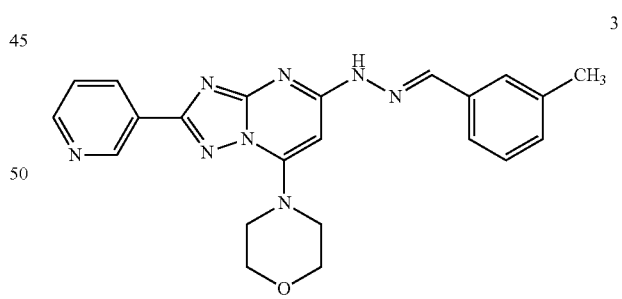

3

Using the procedures described in Example 2, substituting nicotinic acid for iso-nicotinic acid in Step 1, (E)-4-(5-(2-(3-methylbenzylidene)hydrazinyl)-2-(pyridin-3-yl)-[1,2,4]triazole[1,5-a]pyrimidin-7-yl)morpholine is prepared. [M+H]$^+$=415.1

Example 5

Preparation of (E)-4-(5-(2-(3-methoxybenzylidene)hydrazinyl)-2-(pyridin-4-yl)-[1,2,4]triazolo[1,5-a]pyrimidin-7-yl)morpholine (Compound 4)

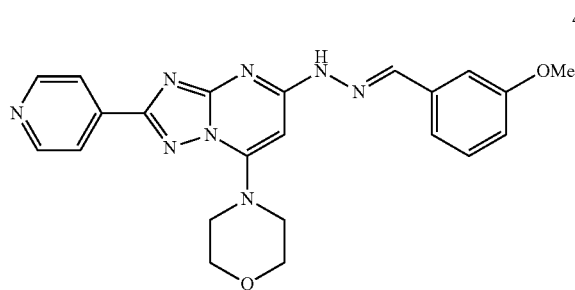

Using the procedures described in Example 2, substituting 3-methoxybenzaldehyde for 3-methylbenzaldehyde in Step 4, (E)-4-(5-(2-(3-methoxybenzylidene)hydrazinyl)-2-(pyridin-4-yl)-[1,2,4]triazolo[1,5-a]pyrimidin-7-yl)morpholine is prepared. [M+H]$^+$=431.1.

Example 6

Preparation of (E)-N-(3-((2-(7-morpholino-2-(pyridin-4-yl)-[1,2,4]triazolo[1,5-a]pyrimidin-5-yl)hydrazono)methyl)phenyl)methanesulfonamide (Compound 5)

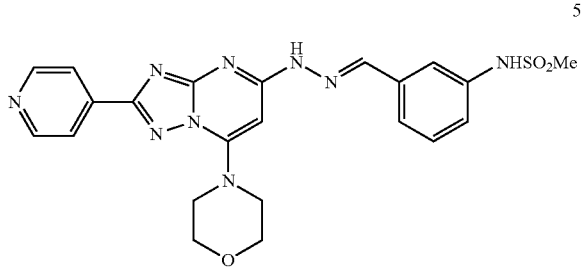

Using the procedures described in Example 2, substituting 2-phenylethylamine for hydrazine in step 4, (E)-N-(3-((2-(7-morpholino-2-(pyridin-4-yl)-[1,2,4]triazolo[1,5-a]pyrimidin-5-yl)hydrazono)methyl)phenyl)methanesulfonamide is prepared. [M+H]$^+$=494.1.

Example 7

Preparation of (E)-4-(5-(2-(3-methylbenzylidene)hydrazinyl)-2-(quinolin-4-yl)-[1,2,4]triazole[1,5-a]pyrimidin-7-yl)morpholine (Compound 6)

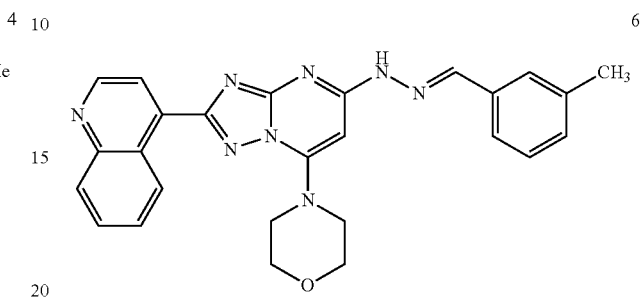

Using the procedures described in Example 2, substituting quinoline-4-carboxylic acid for isonicotinic acid in Step 1, (E)-4-(5-(2-(3-methylbenzylidene)hydrazinyl)-2-(quinolin-4-yl)-[1,2,4]triazolo[1,5-a]pyrimidin-7-yl)morpholine is prepared. [M+H]$^+$=465.1.

Example 8

Preparation of (E)-4-(5-(2-(3-methylbenzylidene)hydrazinyl)-2-(pyrimidin-4-yl)-[1,2,4]triazole[1,5-a]pyrimidin-7-yl)morpholine (Compound 7)

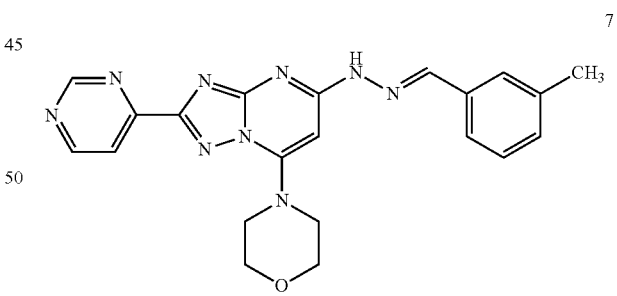

Using the procedures described in Example 2, substituting pyrimidine-4-carboxylic acid for isonicotinic acid in Step 1, (E)-4-(5-(2-(3-methylbenzylidene)hydrazinyl)-2-(pyrimidin-4-yl)-[1,2,4]triazole[1,5-a]pyrimidin-7-yl)morpholine is prepared. [M+H]$^+$=416.1.

Example 9

Preparation of (E)-4-(5-(2-((1H-indol-3-yl)methyl-ene)hydrazinyl)-2-(pyridin-4-yl)-[1,2,4]triazole-[1,5-a]pyrimidin-7-yl)morpholine (Compound 8)

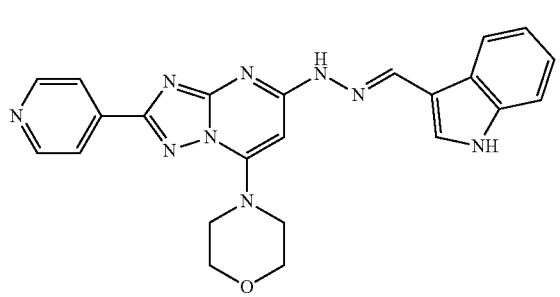

Using the procedures described in Example 2, substituting indole-3-carboxaldehyde for 3-methylbenzaldehyde in Step 4, (E)-4-(5-(2-((1H-indol-3-yl)methylene)hydrazinyl)-2-(pyridin-4-yl)-[1,2,4]triazole[1,5-a]pyrimidin-7-yl)morpholine is prepared. [M+H]$^+$=440.1.

Example 10

Preparation of (E)-4-(5-(2-(pyridin-3-ylmethylene)hydrazinyl)-2-(pyridin-4-yl)-[1,2,4]triazole[1,5-a]pyrimidin-7-yl)morpholine (Compound 9)

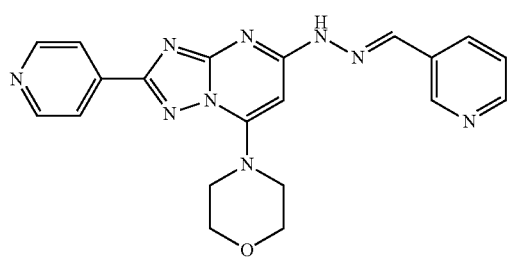

Using the procedures described in Example 2, substituting pyridine-3-carboxaldehyde for 3-methylbenzaldehyde in Step 4, (E)-4-(5-(2-(pyridin-3-ylmethylene)hydrazinyl)-2-(pyridin-4-yl)-[1,2,4]triazole[1,5-a]pyrimidin-7-yl)morpholine is prepared. [M+H]$^+$=402.1.

Example 11

Preparation of (E)-3-((2-(7-morpholino-2-(pyridin-4-yl)-[1,2,4]triazolo[1,5-a]pyrimidin-5-yl)hydrazono)methyl)benzonitrile (Compound 10)

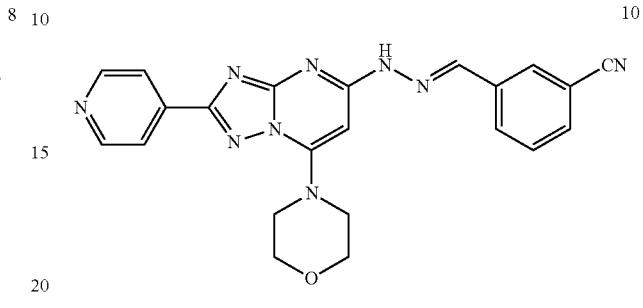

Using the procedures described in Example 2, substituting 3-cyanobenzaldehyde for 3-methylbenzaldehyde in Step 4, (E)-3-((2-(7-morpholino-2-(pyridin-4-yl)-[1,2,4]triazolo[1,5-a]pyrimidin-5-yl)hydrazono)methyl)benzonitrile is prepared. [M+H]$^+$=426.1.

Example 12

Preparation of (E)-4-(5-(2-((6-methoxynaphthalen-2-yl)methylene)hydrazinyl)-2-(pyridin-4-yl)-[1,2,4]triazolo[1,5-a]pyrimidin-7-yl)morpholine (Compound 11)

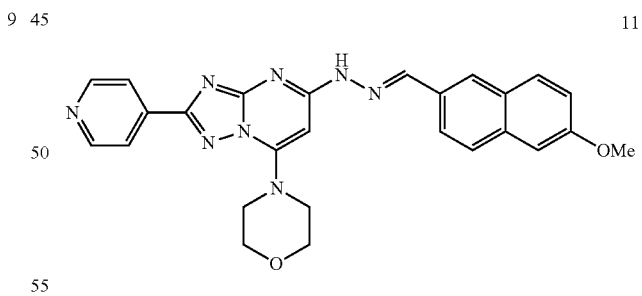

Using the procedures described in Example 2, substituting 6-methoxy-2-naphthaldehyde for 3-methylbenzaldehyde in Step 4, (E)-4-(5-(2-((6-methoxynaphthalen-2-yl)methylene)hydrazinyl)-2-(pyridin-4-yl)-[1,2,4]triazolo[1,5-a]pyrimidin-7-yl)morpholine is prepared. [M+H]$^+$=481.1.

Example 13

Preparation of (E)-4-(5-(2-(3-isopropylbenzylidene)hydrazinyl)-2-(pyridin-4-yl)-[1,2,4]triazolo[1,5-a]pyrimidin-7-yl)morpholine (Compound 12)

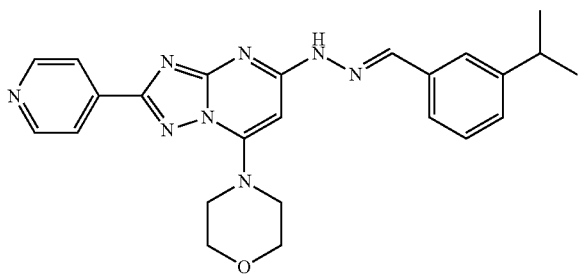

Using the procedures described in Example 2, substituting 3-isopropylbenzaldehyde for 3-methylbenzaldehyde in Step 4, (E)-4-(5-(2-(3-isopropylbenzylidene)hydrazinyl)-2-(pyridin-4-yl)-[1,2,4]triazolo[1,5-a]pyrimidin-7-yl)morpholine is prepared. [M+H]$^+$=443.1.

Example 14

PIKfyve Inhibitor APY0201 Selectively Inhibits Growth of Cancer Cell Lines

Viability of several cancer cell lines was assessed in the presence of two compounds: PIKfyve inhibitor APY0201, and Dinaciclib (CDK inhibitor, also known to the knowledgeable in art as a potent inhibitor of cancer cell growth). Three cancer cell lines, multiple myeloma KMS12E, Non-Hodgkin's lymphoma SU-DHL4, T-cell lymphoma Hut-78, and normal human peripheral blood mononuclear cells derived from healthy individual were tested. The cells were plated in 384 well plates in RPMI medium supplemented with 10% fetal bovine serum. Cancer cells were plated at 1000 cells/well and normal cells at 10,000 cells per well in a total volume of 30 uL/well. Immediately after plating, the test compounds were added at five concentrations: 10 uM-1 uM-0.01 uM-0.001 uM, in duplicate wells for each concentration. The cells were exposed to compounds for 70 hours at 37° C. in humidified incubator with 5% CO2. Cell viability was determined by Presto Blue reagent (Thermo Scientific/Invitrogen). Dinaciclib inhibited viability of all cell types with similar potency (IC50: 10 nM-15 nM). PIKfyve inhibitor APY0201 potently inhibited viability of the three cancer cell lines (IC50: 33 nM-46 nM) but, unlike Dinaciclib, it did not significantly inhibit viability of normal PBMCs (IC50>10 uM), demonstrating >100 fold selectivity towards cancer cells over normal cells. See FIG. 1A-1D.

Similarly, viability of cancer cell lines: T-cell lymphoma Hut-78 multiple myeloma KMS12E, as well as normal human peripheral blood mononuclear cells were assessed in the presence of apilimod, APY0201, Compound 1 (described in Example 2 of the present disclosure) and YM201636. Apilimod, APY0201 and Compound 1 showed selectivity towards cancer cells over normal cells:

| PIKFYVE Inhibitor | T-cell Lymphoma, IC50 (mM) | Plasma cell myeloma, IC50 (mM) | Normal human PBMCs, IC50 (mM) |
|---|---|---|---|
| Apilimod | 0.027 | 0.073 | >10 |
| APY0201 | 0.028 | 0.074 | >10 |
| Compound 1 | 0.047 | 0.115 | >10 |
| YM201636 | 0.676 | 0.781 | 1.44 |

Figure 5A:
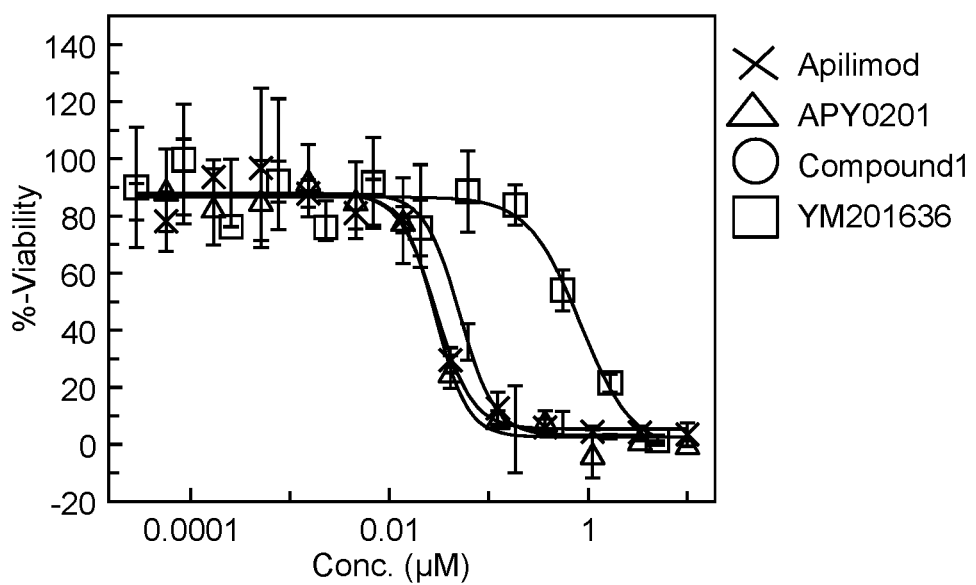
FIG. 5A-5C show dose responsive curves for apilimod, APY 0201, Compound 1 of the present disclosure, and YM201636 against different blood cancer cell lines and in normal human peripheral blood mononuclear cells (PBMCs).
Figure 5B:
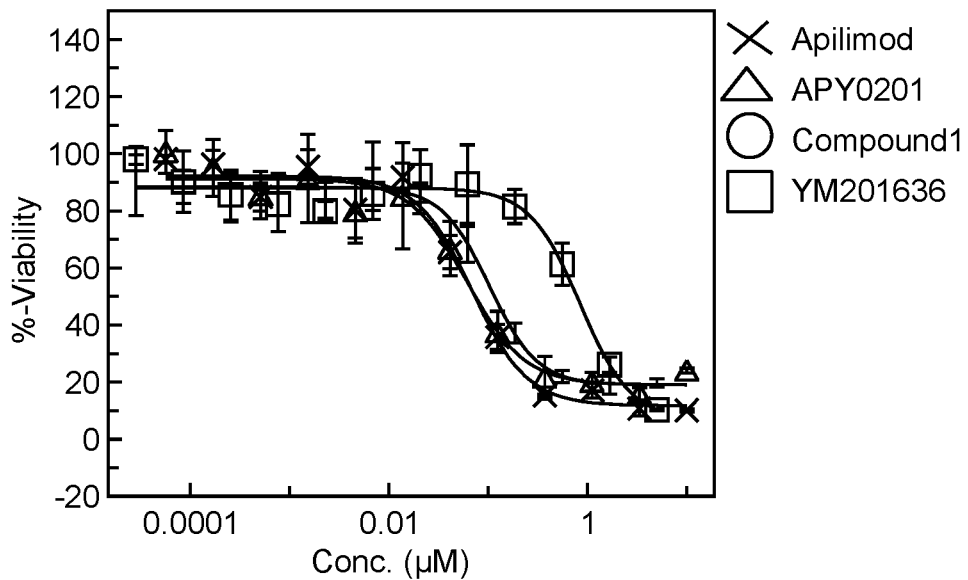
Figure 5C:
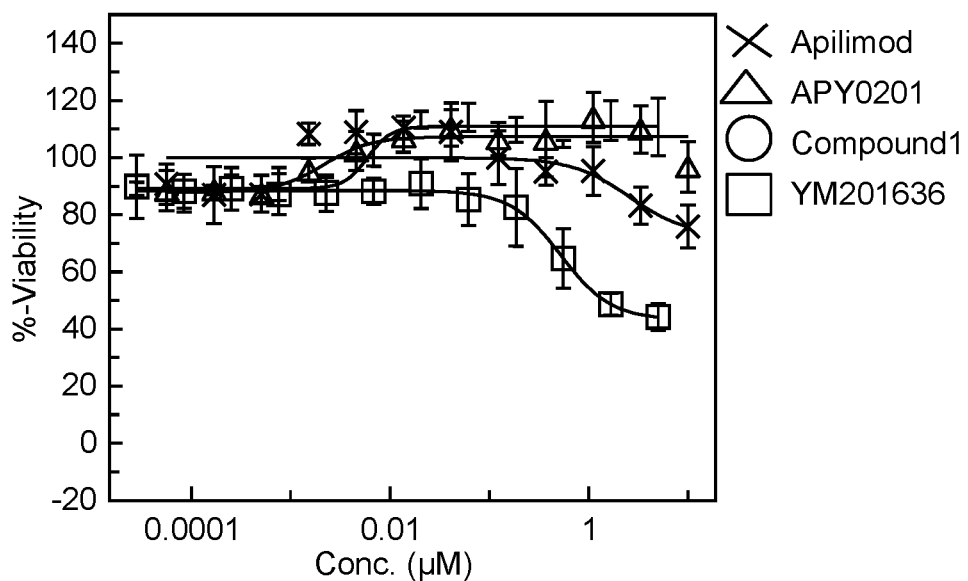

Also see FIG. 5A-C.

Example 15

Figure 2A:
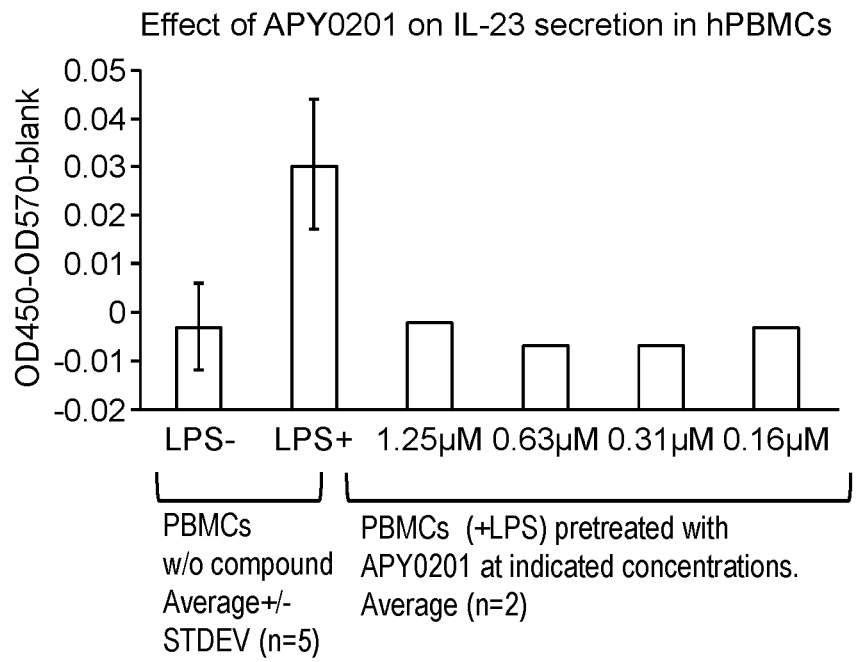
FIG. 2A-2B show that both APY0201 and Compound 1 of the present disclosure blocked secretion of IL-23.
Figure 2B:
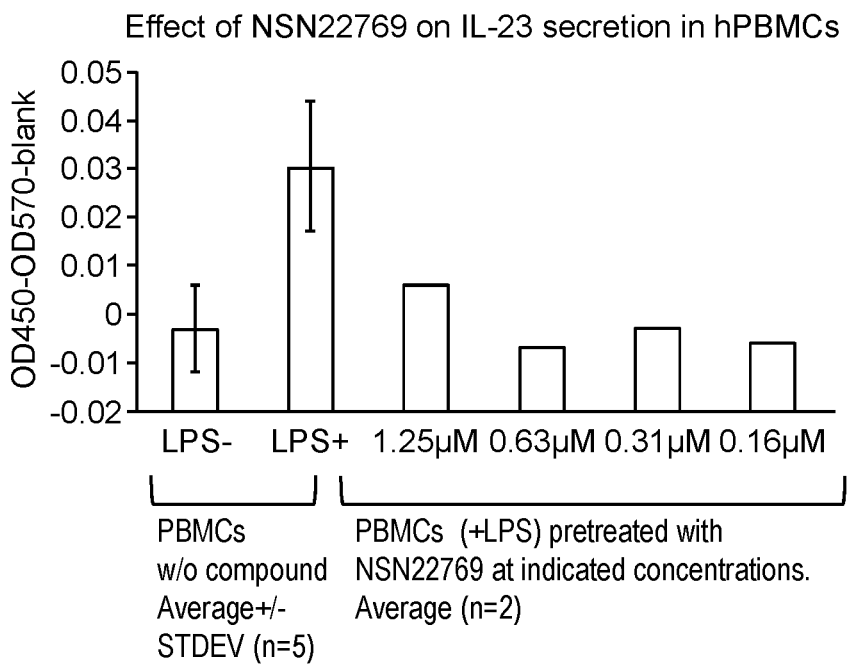

Effect of PIKfyve Inhibitor APY0201 and Compound 1 (Described in Example 2 of the Present Disclosure) on IL23 Secretion by Normal Human Peripheral Monocytes Stimulated with LPS Human PBMCs were plated in 96 well plate at a density of 150,000 cells per a well in RPMI medium supplemented with 10% FBS. The cells were pre-incubated with compounds for 2 h. Following pre-incubation, the cells were stimulated with 100 ng/mL LPS for 18 hours. The secreted IL-23 was determined by ELISA (Human IL-23 Quantikine ELISA Kit, R&D cat #D2300B). Conclusion: APY0201 and Compound 1 (designated as NSN22769) completely blocked secretion of IL-23 by the LPS-induced PBMCs. See FIGS. 2A and 2B.

Example 16

Figure 3A:
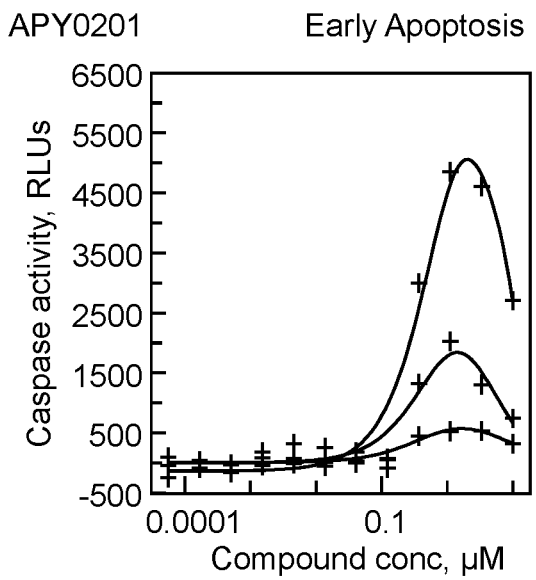
FIG. 3A-3C show that APY0201, apilimod, and Compound 1 of the present disclosure induce apoptosis in ML-2 cancer cell line.
Figure 3B:
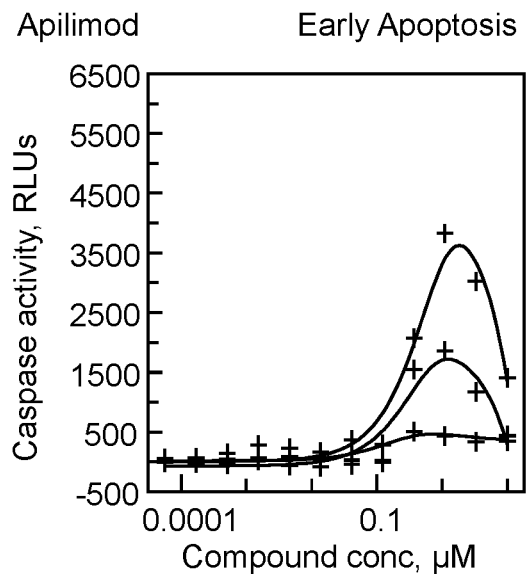
Figure 3C:
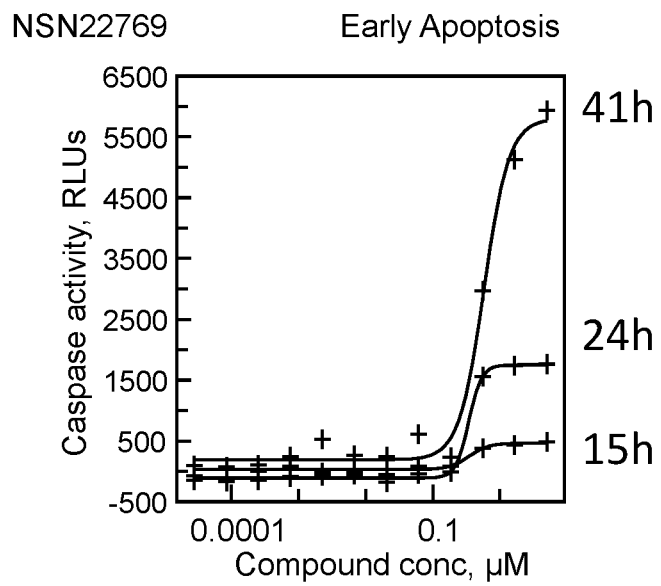

PIKfyve Inhibitors and Compound 1 (Described in Example 2 of the Present Disclosure) Induce Apoptosis in ML-2 Cancer Cell Line Acute myelomonocytic leukemia cells ML-2 were plated in 96 well plate at a density of 50,000 cells per a well in RPMI medium supplemented with 10% FBS. The cells were exposed to compounds and the early apoptosis marker, Caspase3/7 activity, was measured in the cells at 15 h, 24 h and 41 h after exposure to compounds. The caspase activity was determined using Caspase-Glo® 3/7 Assay (Promega) and according to the protocol provided by the manufacturer. Conclusion: all three compounds including Compound 1 (designated as NSN22769) triggered Caspase3/7 activation in ML-2 cells—a hallmark of early apoptosis. See FIG. 3A-3C.

Example 17

Biochemical PIKfyve Assay

Full length human recombinant PIKFYVE expressed in baculovirus expression system as N-terminal GST-fusion protein (265 kDa) was obtained from Cama Biosciences (Kobe, Japan). Bodipy-labeled phosphatidylinositol 3-phosphate (PI3P) was obtained from Echelon Biosciences (Salt Lake City, Utah USA). 1,2-dioctanoyl-sn-glycero-3-phospho-L-serine (PS) was purchased from Avanti Polar Lipids (Alabaster, Ala. US).

PI3P/PS substrate was prepared as following: 10 mM stock of PS was prepared in chloroform in glass container. 1 mM PI3P stock was prepared in 50 mM HEPES, pH 7.5. Prior to experiment, the PS stock was quickly evaporated under a flow of nitrogen and the dry pellet was re-suspended in 50 mM HEPES, pH 7.5 to a final concentration of 20 uM. The re-suspended PS was mixed with PI3P at 10:1 molar ratio: 10 uM PS and 1 uM PIP2. The prepared PI3P/PS mix was sonicated in ultrasound water bath for 15 min (3 times, 5 min each).

The kinase reactions were assembled in 384 well plates (Greiner) in a total volume of 20 μL as following: The kinase protein was pre-diluted in the assay buffer comprising: 25 mM HEPES, pH 7.5, 1 mM DTT, 2.5 mM MgCl$_2$ and 2.5 mM MnCl$_2$, 0.005% Triton X-100 and dispensed into 384 well plate (10 μL per well). The test compounds were serially pre-diluted in DMSO and added to the protein samples by acoustic dispensing (Labcyte Echo). Concentration of DMSO was equalized to 1% in all samples. All test compounds were tested at 12 concentrations in triplicate. The control samples (0%-inhibition in the absence of inhibitor, DMSO only) and 100%-inhibition (in the absence of enzyme) were assembled in replicates of four and were used to calculate %-inhibition in the presence of compounds. The reactions were initiated by addition of 10 μL of the PI3P/PS substrate supplemented with ATP. Final concentration of enzymes was: 2 nM Final concentration of ATP was: 10 μm. The kinase reactions were allowed to proceed for 3 h at room temperature. Following incubation, the reactions were quenched by addition of 50 μL of termination buffer (100 mM HEPES, pH 7.5, 0.01% Triton X-100, 20 mM EDTA). Terminated plates were analyzed on a microfluidic electrophoresis instrument (Caliper LabChip® 3000, Caliper Life Sciences/Perkin Elmer). A change in the relative fluorescence intensity of the PI(3)P substrate and PI(3,5)P product peaks was the parameter measured. Activity in each test sample was determined as the product to sum ratio (PSR): P/(S+P), where P is the peak height of the product, and S is the peak height of the substrate.

Percent inhibition ($P_{inh}$) was determined using the following equation: $P_{inh}=(PSR_{0\% inh}-PSR_{compound})/(PSR_{0\% inh}-PSR_{100\% inh})*100$, in which: $PSR_{compound}$ is the product/sum ratio in the presence of compound, $PSR_{0\% inh}$ is the product/sum ratio in the absence of compound and the $PSR_{100\% inh}$ is the product/sum ratio in the absence of the enzyme. To determine IC50 of compounds (50%-inhibition) the %-inh cdata ($P_{inh}$ versus compound concentration) were fitted by a 4 parameter sigmoid dose-response model using XLfit software (IDBS).

Figure 4:
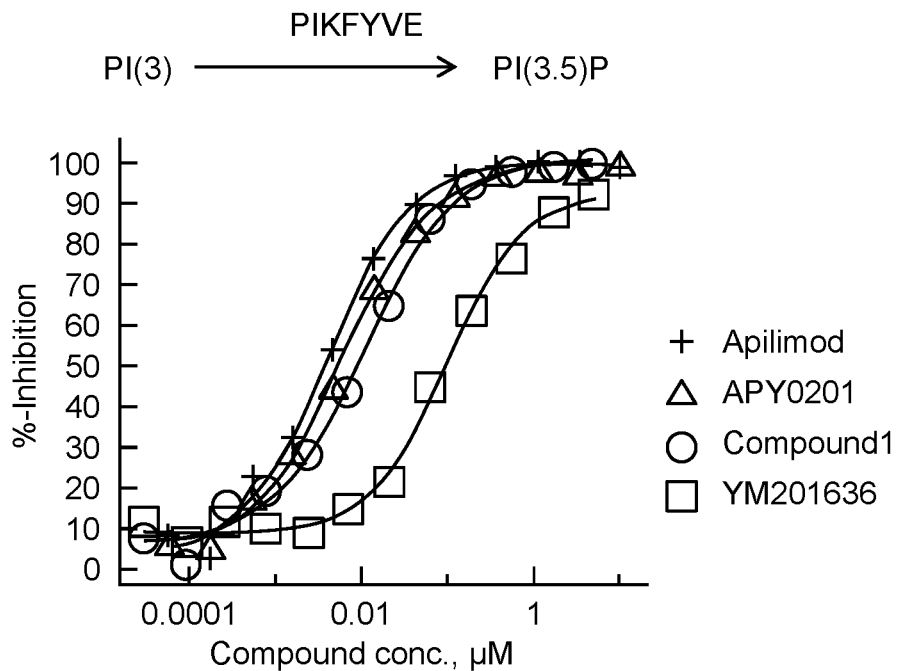
FIG. 4 shows the dose responsive curves for apilimod, APY 0201, Compound 1 of the present disclosure, and YM201636 in PIKfyve kinase inhibition assay.

Apilimod, APY0201, Compound 1 (described in Example 2 of the present disclosure) of the present disclosure, and YM201636 were tested for their ability to inhibit PIKfyve kinase in this assay. The results are shown in FIG. 4 and in the table below:

| Tested Compound | PIKfyve IC50, (μM) |
|---|---|
| Apilimod | 0.004 |
| APY0201 | 0.006 |
| Compound 1 | 0.01 |
| YM201636 | 0.098 |

What is claimed is:

1. A compound of Formula I or a pharmaceutically acceptable salt thereof:

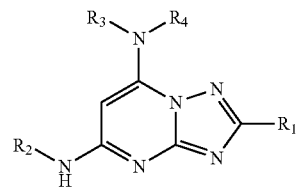

Formula I wherein
  $R_1$ is optionally substituted alkyl, optionally substituted cycloalkyl, optionally substituted heterocyclyl, optionally substituted aryl, or optionally substituted heteroaryl, provided $R_1$ is not cyclohexyl,
  $R_2$ is alkyl, aryl, heteroaryl, —N=CH-alkyl, —N=CH-aryl or —N=CH-heteroaryl, in which each of the alkyl, aryl and heteroaryl is optionally substituted,
  $R_3$ and $R_4$ together with the nitrogen to which they are attached form a mono or bi-cyclic heterocyclyl or a bi-cyclic aryl, each of the mono, bi-cyclic heterocyclyl and bi-cyclic aryl is optionally substituted with one, two, three, or four groups selected from lower alkyl.

2. The compound of claim 1 and/or a pharmaceutically acceptable salt thereof, which is a compound of Formula II and/or a pharmaceutically acceptable salt thereof:

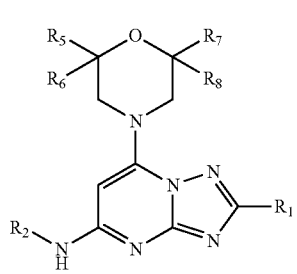

Formula II wherein
  $R_1$ is optionally substituted alkyl, optionally substituted cycloalkyl, optionally substituted heterocyclyl, optionally substituted aryl, or optionally substituted heteroaryl, provided $R_1$ is not cyclohexyl,
  $R_2$ is optionally substituted alkyl, optionally substituted aryl, optionally substituted heteroaryl, N=CH-alkyl, N=CH-aryl or N=CH-heteroaryl in which alkyl, aryl and heteroaryl can be optionally substituted,
  $R_5$, $R_6$, $R_7$, and $R_8$ are independently H or methyl.

3. The compound of claim 1 and/or a pharmaceutically acceptable salt thereof, which is a compound of Formula III and/or a pharmaceutically acceptable salt thereof:

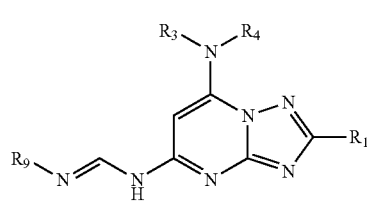

Formula III wherein
R₁ is optionally substituted alkyl, optionally substituted cycloalkyl, optionally substituted heterocyclyl, optionally substituted aryl, or optionally substituted heteroaryl, provided R₁ is not cyclohexyl,
R₉ is optionally substituted alkyl, optionally substituted aryl, or optionally substituted heteroaryl,
R₃ and R₄ together with the nitrogen to which they are attached form an optionally substituted heterocyclyl.

4. The compound of claim 1 and/or a pharmaceutically acceptable salt thereof, wherein R₁ is optionally substituted phenyl, optionally substituted lower alkyl, optionally substituted mono-cyclic heteroaryl, or optionally substituted mono-cyclic heterocyclyl.

5. The compound of claim 1 and/or a pharmaceutically acceptable salt thereof, wherein R₁ is a phenyl optionally substituted with one or two groups selected from —F, —Cl, —CN, —OH, —C(O)NH₂, —CF₃, —NH₂, —NHSO₂-lower alkyl, —OCF₃, —O-lower alkyl, and lower alkyl.

6. The compound of claim 1 and/or a pharmaceutically acceptable salt thereof, wherein R₁ is a pyridinyl optionally substituted with one or two groups selected from —F, —Cl, —CN, —OH, —C(O)NH₂, —CF₃, NH₂, —NHSO₂-lower alkyl, —OCF₃, —O-lower alkyl, and lower alkyl.

7. The compound of claim 1 and/or a pharmaceutically acceptable salt thereof, wherein R₁ is a pyrimidinyl optionally substituted with one or two groups selected from —F, —Cl, —CN, —OH, —C(O)NH₂, —CF₃, —NH₂, —NHSO₂-lower alkyl, —OCF₃, —O-lower alkyl, and lower alkyl.

8. The compound of claim 1 and/or a pharmaceutically acceptable salt thereof, wherein R₁ is quinolinyl or isoquinolinyl optionally substituted with one or two groups selected from —F, —Cl, —CN, —OH, —C(O)NH₂, —CF₃, —NH₂, —NHSO₂-lower alkyl, —OCF₃, —O-lower alkyl, and lower alkyl.

9. The compound of claim 1 and/or a pharmaceutically acceptable salt thereof, wherein R₁ is a lower alkyl optionally substituted with one or two groups selected from —F, —Cl, —CN, —OH, —C(O)NH₂, —CF₃, —NH₂, —OCF₃, —O-lower alkyl, lower alkyl, phenyl, and mono-cyclic heteroaryl.

10. The compound of claim 1 and/or a pharmaceutically acceptable salt thereof, wherein R₁ is azetidinyl, oxetanyl, tetrahydrofuran, or pyrrolidinyl, each of which is optionally substituted with one or two groups selected from —F, —Cl, —CN, —OH, —C(O)NH₂, —CF₃, —NH₂, —OCF₃, —O-lower alkyl, and lower alkyl.

11. The compound of claim 1 and/or a pharmaceutically acceptable salt thereof, wherein R₂ is N=CH-aryl, —N=CH-heteroaryl, or N=CH-alkyl, each of aryl, heteroaryl, and alkyl is optionally substituted with one or two groups selected from —F, —Cl, —CN, —OH, —C(O)NH₂, —CF₃, —NH₂, —NHSO₂-lower alkyl, —OCF₃, —O-lower alkyl, lower alkyl, phenyl, and mono-cyclic heteroaryl.

12. The compound of claim 1 and/or a pharmaceutically acceptable salt thereof, wherein R₂ is —N=CH-phenyl, —N=CH-naphthalenyl, —N=CH-pyridinyl, —N=CH-indolyl, or —N=CH-lower alkyl, each of phenyl, naphthalenyl, pyridinyl, indolyl and lower alkyl is optionally substituted with one or two groups selected from —F, —Cl, —CN, —OH, —C(O)NH₂, —CF₃, —NH₂, —NHSO₂-lower alkyl, —OCF₃, —O-lower alkyl, lower alkyl, phenyl, and mono-cyclic heteroaryl.

13. The compound of claim 1 and/or a pharmaceutically acceptable salt thereof, wherein the mono-cyclic heterocyclyl is aziridine, azetidine, pyrolidine, piperidine, morpholine, piperazine, thiomorpholine, thiomorpholine-S-oxide, thiomorpholine-S,S-dioxide, azepane, 1,4-oxazepane, or 1,4-thiazepane.

14. The compound of claim 3 and/or a pharmaceutically acceptable salt thereof, wherein R₉ is aryl, heteroaryl, or alkyl each of which is optionally substituted with one or two groups selected from —F, —Cl, —CN, —OH, —C(O)NH₂, —CF₃, —NH₂, —NHSO₂-lower alkyl, —OCF₃, —O-lower alkyl, lower alkyl, phenyl, and mono-cyclic heteroaryl.

15. The compound of claim 3 and/or a pharmaceutically acceptable salt thereof, wherein R₉ is phenyl, naphthalenyl, pyridinyl, indolyl, or lower alkyl, each of phenyl, naphthalenyl, pyridinyl, indolyl and lower-alkyl is optionally substituted with one or two groups selected from —F, —Cl, —CN, —OH, —C(O)NH₂, —CF₃, —NH₂, —NHSO₂-lower alkyl, —OCF₃, —O-lower alkyl, lower alkyl, phenyl, and mono-cyclic heteroaryl.

16. The compound of claim 1 and/or a pharmaceutically acceptable salt thereof, wherein R₁ is

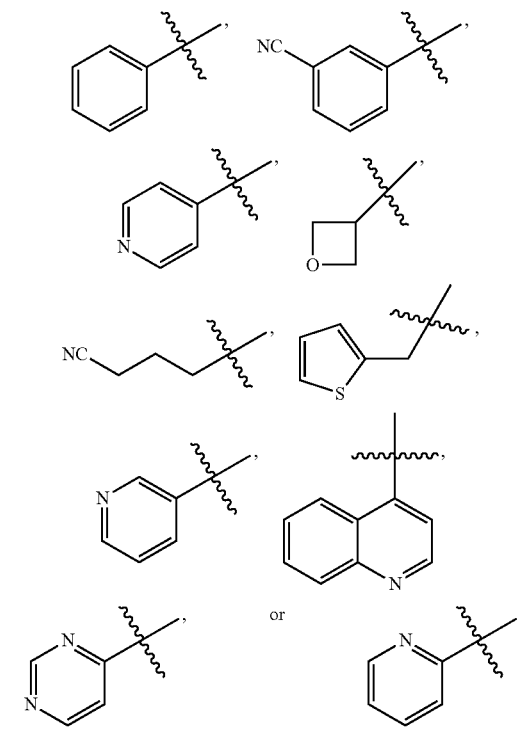

wherein ⌇ indicates the point of attachment to the remaining moiety of the molecule.

17. The compound of claim 1 and/or a pharmaceutically acceptable salt thereof, wherein R₂ is

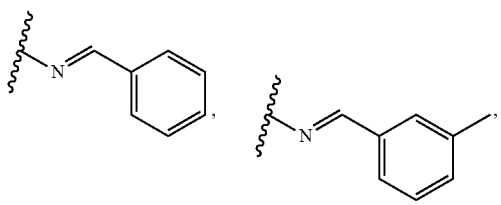

-continued

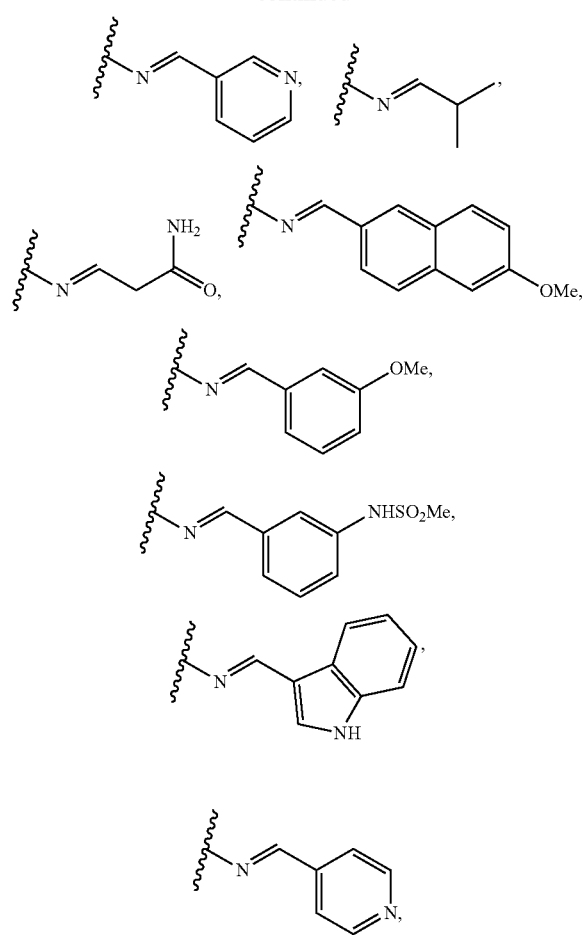

wherein ⌇ indicates the point of attachment to the remaining moiety of the molecule.

18. The compound of claim 1 and/or a pharmaceutically acceptable salt thereof, wherein $R_3$ and $R_4$ together with the nitrogen to which they are attached form one of the following rings:

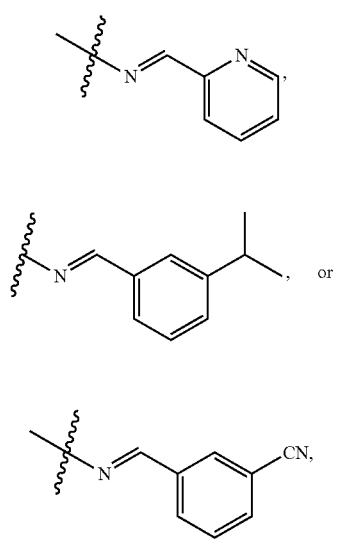

wherein ⌇ indicates the point of attachment to the remaining moiety of the molecule.

19. The compound of claim 1 and/or a pharmaceutically acceptable salt thereof is selected from the following compounds:

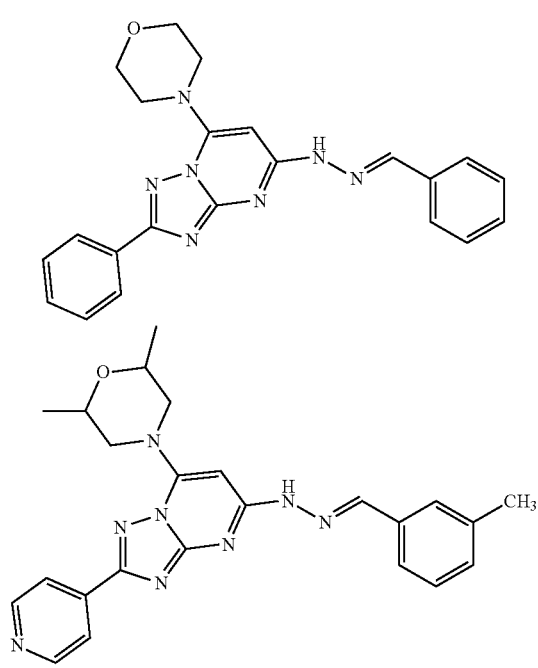

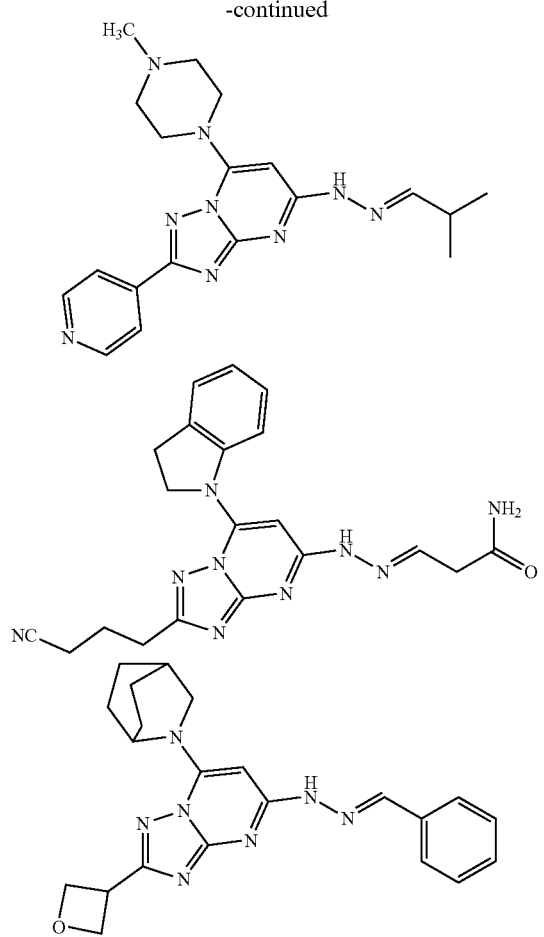
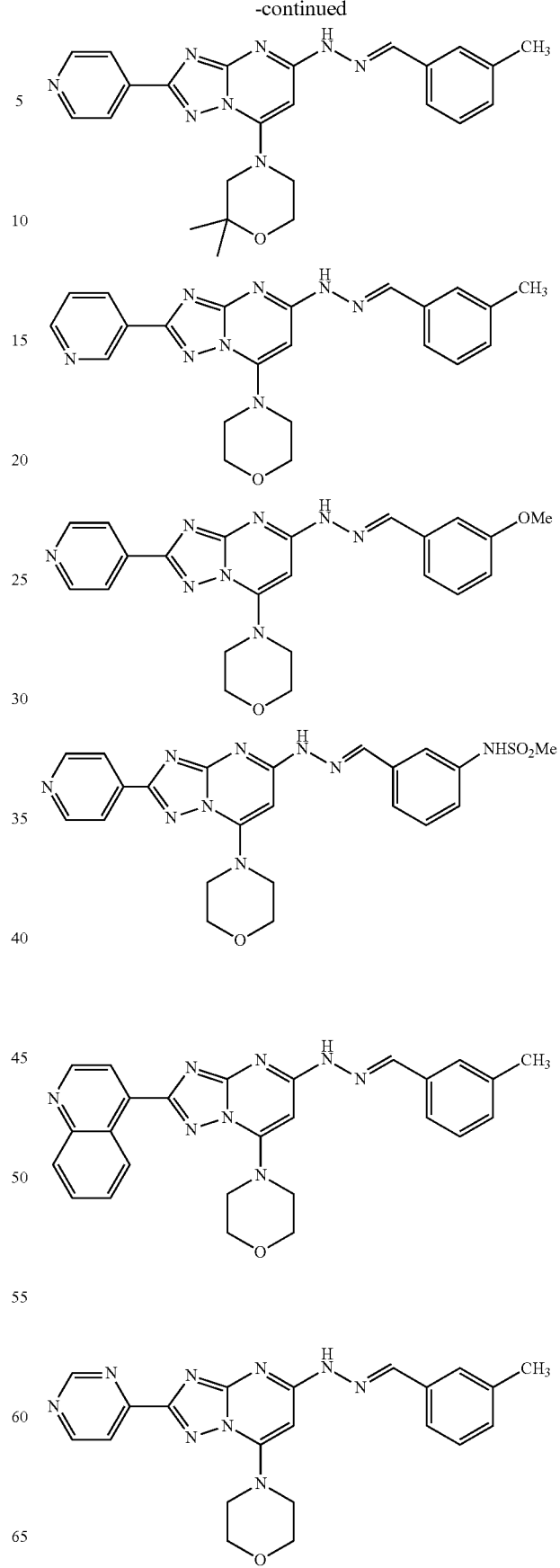

43
-continued
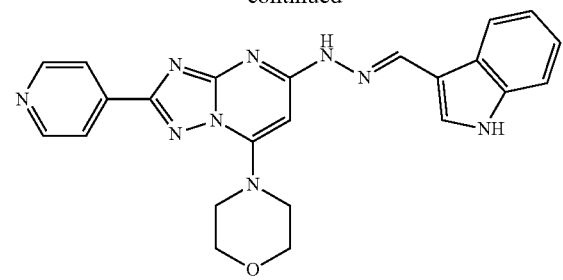
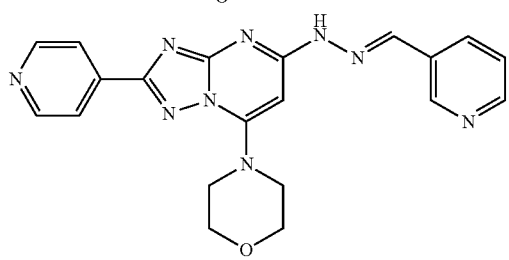
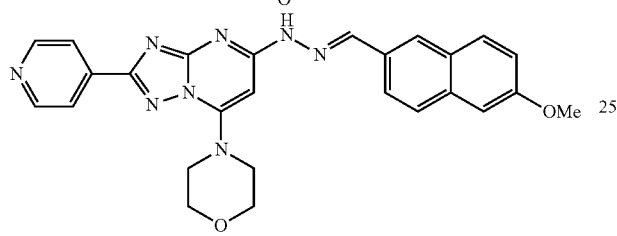
44
-continued
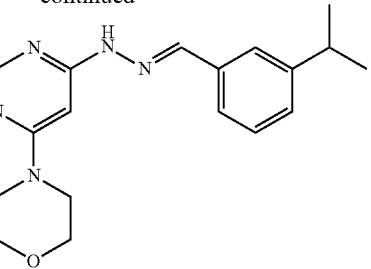
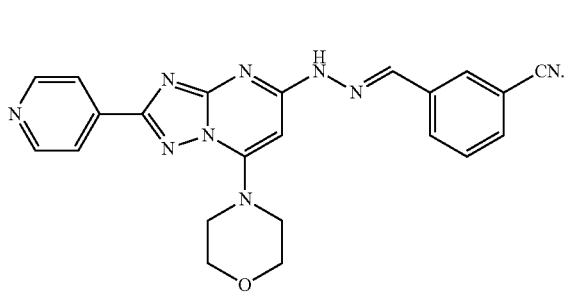 [SMILES: N#Cc1cccc(/C=N/Nc2cc(N3CCOCC3)n3nc(-c4ccncc4)nc3n2)c1]
20. A pharmaceutical composition comprising a compound of claim 1 and/or a pharmaceutically acceptable salt thereof and a pharmaceutically acceptable carrier.
* * * * *